United States Patent [19]

Meyer et al.

[11] Patent Number: 5,563,114
[45] Date of Patent: Oct. 8, 1996

[54] CYCLOHEXENONE OXIME ETHERS, THEIR PREPARATION, INTERMEDIATES FOR THEIR PREPARATION AND THEIR USE AS HERBICIDES

[75] Inventors: Norbert Meyer, Ladenburg; Juergen Kast, Boehl-Iggelheim; Ulf Misslitz, Neustadt; Albrecht Harreus, Ludwigshafen; Norbert Goetz, Worms; Bruno Wuerzer, Otterstadt; Helmut Walter, Obrigheim; Karl-Otto Westphalen, Speyer; Matthias Gerber, Mutterstadt, all of Germany

[73] Assignee: BASF Aktiengesellschaft, Ludwigshafen, Germany

[21] Appl. No.: 409,969

[22] Filed: Mar. 24, 1995

Related U.S. Application Data

[63] Continuation of Ser. No. 697,180, May 8, 1991, abandoned.

[30] Foreign Application Priority Data

May 9, 1990 [DE] Germany .......................... 40 14 983.8

[51] Int. Cl.⁶ .......................... A01N 43/16; A01N 43/28; A01N 43/78; A01N 43/18
[52] U.S. Cl. .......................... 504/288; 504/266; 504/289; 504/290; 504/294; 504/292; 504/295; 504/344; 548/204; 549/13; 549/39; 549/77; 549/426; 549/451; 549/496; 564/256
[58] Field of Search .................. 549/13, 39, 77, 549/426, 451, 496; 504/288, 266, 289, 290, 294, 292, 295, 344; 564/256

[56] References Cited

U.S. PATENT DOCUMENTS

| | | | |
|---|---|---|---|
| 4,249,937 | 2/1981 | Iwataki et al. | 71/97 |
| 4,440,566 | 4/1984 | Luo | 71/98 |
| 4,624,696 | 11/1986 | Keil et al. | 71/88 |
| 4,654,073 | 3/1987 | Jahn et al. | 71/88 |
| 4,692,553 | 9/1987 | Keil et al. | 564/185 |
| 4,880,456 | 11/1989 | Kolassa et al. | 71/88 |
| 4,898,610 | 2/1990 | Keil et al. | 71/121 |
| 5,022,914 | 6/1991 | Kast et al. | 71/88 |
| 5,364,833 | 11/1994 | Kast et al. | 504/289 |

FOREIGN PATENT DOCUMENTS

| | | |
|---|---|---|
| 080301 | 11/1981 | Australia . |
| 125094 | 11/1984 | Australia . |
| 0080301 | 6/1983 | European Pat. Off. . |
| 0218233 | 4/1987 | European Pat. Off. . |
| 0368227 | 5/1990 | European Pat. Off. . |
| 137174 | 4/1985 | Germany . |
| 142741 | 5/1985 | Germany . |
| 169521 | 1/1986 | Germany . |
| 177913 | 4/1986 | Germany . |
| 218233 | 4/1987 | Germany . |
| 238021 | 9/1987 | Germany . |

Primary Examiner—Peter O'Sullivan
Attorney, Agent, or Firm—Keil & Weinkauf

[57] ABSTRACT

Cyclohexenone oxime ethers of the general formula I

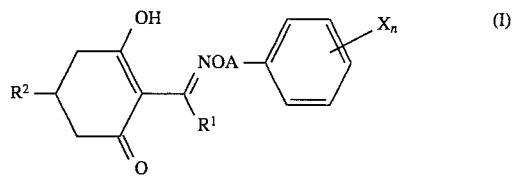

where
$R^1$ is alkyl,
A is unsubstituted or substituted $C_3$-, $C_5$- or $C_6$-alkylene or $C_3$-, $C_5$- or $C_6$-alkenylene,
X is $NO_2$, CN, halogen, alkyl, alkoxy, phenoxy, alkylthio, haloalkyl, haloalkoxy, carboxyl, alkoxycarbonyl, unsubstituted or substituted benzyloxycarbonyl and/or unsubstituted or substituted phenyl,
n is 0–3 or 1–5 where X is halogen,
$R^2$ is alkoxy-alkyl or alkylthio-alkyl, unsubstituted or substituted cycloalkyl or cycloalkenyl, an unsubstituted or substituted 5-membered saturated heterocyclic structure having one or two oxygen and/or sulfur atoms as hetero atoms, an unsubstituted or substituted 6-membered or 7-membered heterocyclic structure having up to two oxygen and/or sulfur atoms and up to two double bonds, an unsubstituted or substituted 5-membered heteroaromatic having up to two nitrogen atoms and one oxygen atom or one sulfur atom, or unsubstituted or substituted phenyl or pyridyl, and their agriculturally useful salts and esters of $C_1$–$C_{10}$-carboxylic acids and inorganic acids, processes and intermediates for their preparation, and their use as herbicides.

3 Claims, No Drawings

CYCLOHEXENONE OXIME ETHERS, THEIR PREPARATION, INTERMEDIATES FOR THEIR PREPARATION AND THEIR USE AS HERBICIDES

This application is a continuation of application Ser. No. 07/697,180, filed on May 8, 1991 now abandoned.

The present invention relates to novel herbicidal cyclohexenone oxime ethers of the formula I

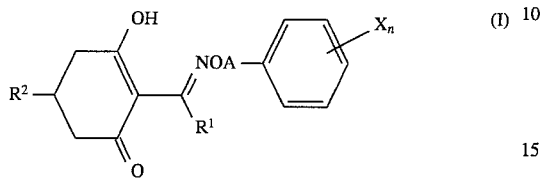

where $R^1$ is $C_1-C_6$-alkyl;

A is a $C_3$-, $C_5$- or $C_6$-alkylene or $C_3$-, $C_5$- or $C_6$-alkenylene chain, where these chains may carry from one to three $C_1-C_3$-alkyl groups and/or halogen atoms or one methylene group;

X is nitro, cyano, halogen, $C_1-C_4$-alkyl, $C_1-C_4$-alkoxy, phenoxy-$C_1-C_4$-alkylthio, $C_1-C_4$-haloalkyl, $C_1-C_4$-haloalkoxy, carboxyl, $C_1-C_4$-alkoxycarbonyl, benzyloxycarbonyl and/or phenyl, where the aromatic substituents may also carry from one to three radicals selected from the group consisting of nitro, cyano, halogen, $C_1-C_4$-alkyl, $C_1-C_4$-alkoxy, $C_1-C_4$-alkylthio, $C_1-C_4$-haloalkyl, $C_1-C_4$-haloalkyloxy, carboxyl, $C_1-C_4$-alkoxycarbonyl and benzyloxycarbonyl or $C_1-C_4$-alkoxy-$C_1-C_6$-alkyl;

n is from 0 to 3, or 1 to 5 where X is halogen;

$R^2$ is $C_1-C_4$-alkoxy-$C_1-C_6$-alkyl or $C_1-C_4$-alkylthio-$C_1-C_6$-alkyl;

$C_3-C_7$-cycloalkyl or $C_5-C_7$-cycloalkenyl, where these groups may carry from one to three radicals selected from the group consisting of $C_1-C_4$-alkyl, $C_1-C_4$-alkoxy, $C_1-C_4$-alkylthio, $C_1-C_4$-haloalkyl, hydroxyl and halogen;

a 5-membered saturated heterocyclic structure which contains one or two hetero atoms selected from the group consisting of oxygen and sulfur and may also carry from one to three radicals selected from the group consisting of $C_1-C_4$-alkyl, $C_1-C_4$-alkoxy, $C_1-C_4$-alkylthio and $C_1-C_4$-haloalkyl;

a saturated or partially or completely unsaturated 6-membered or 7-membered heterocyclic structure containing one or two hetero atoms selected from the group consisting of oxygen and sulfur, where the heterocyclic structure may also carry from one to three radicals selected from the group consisting of hydroxyl, halogen, $C_1-C_4$-alkyl, $C_1-C_4$-alkoxy, $C_1-C_4$-alkylthio and $C_1-C_4$-haloalkyl, a 5-membered heteroaromatic structure containing one or two nitrogen atoms and one oxygen atom or one sulfur atom, where this ring may also carry from one to three radicals selected from the group consisting of halogen, cyano, $C_1-C_4$-alkyl, $C_1-C_4$-alkoxy, $C_1-C_4$-alkylthio, $C_1-C_4$-haloalkyl, $C_2-C_6$-alkenyl, $C_2-C_6$-alkenyloxy, $C_2-C_6$-haloalkenyl and $C_1-C_4$-alkoxy-$C_1-C_4$-alkyl, or phenyl or pyridyl, where these groups may also carry from one to three radicals selected from the group consisting of halogen, nitro, cyano, $C_1-C_4$-alkyl, $C_1-C_4$-alkoxy, $C_1-C_4$-alkylthio, $C_1-C_4$-haloalkyl, $C_3-C_6$-alkenyloxy, $C_3-C_6$-alkynyloxy and $-NR^3R^4$, where $R^3$ is hydrogen, $C_1-C_4$-alkyl, $C_3-C_6$-alkenyl or $C_3-C_6$-alkynyl and $R^4$ is hydrogen, $C_1-C_4$-alkyl, $C_3-C_6$-alkenyl, $C_3-C_6$-alkynyl, $C_1-C_6$-acyl or benzoyl, where the aromatic ring may also carry from one to three radicals selected from the group consisting of nitro, cyano, halogen, $C_1-C_4$-alkyl, $C_1-C_4$-alkoxy, $C_1-C_4$-alkylthio and $C_1-C_4$-haloalkyl, and their agriculturally useful salts and esters of $C_1-C_{10}$-carboxylic acids and inorganic acids.

The present invention furthermore relates to a process and intermediates for their preparation and their use as crop protection agents.

The novel cyclohexenones I are evidently acidic, ie. they can form simple reaction products, such as salts of alkali metal or alkaline earth metal compounds or enol esters.

The compounds of the formula I can occur in a plurality of tautomeric forms, all of which are embraced by the claims.

The literature describes cyclohexenones of the general formula I'

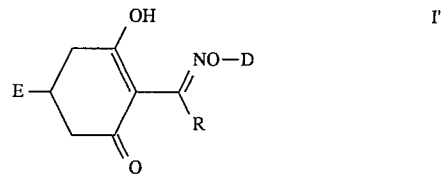

where, inter alia,

D is benzyl and E is 2-ethylthiopropyl (U.S. Pat. No. 4,440,566),

D is benzyl or but-2-enyl and E is a substituted 5-membered hetaryl radical (EP-A 238 021 and EP-A 125 094), D is benzyl or but-2-enyl and E is substituted phenyl (EP-A 80 301) or D is but-2-enyl and E is a 5-membered to 7-membered heterocyclic ring having up to two O or S atoms and up to two double bonds (EP-A 218 233), as herbicides.

It is an object of the present invention to provide compounds which have high selectivity at a low application rate, ie. control undesirable plants without damaging the crops.

We have found that this object is achieved by the novel cyclohexenone oxime ethers of the formula I, which have a good herbicidal action, preferably against species from the family consisting of the grasses (Gramineae). They are tolerated by, and therefore selective in, broad-leaved crops and monocotyledon crops which do not belong to the Gramineae. They also include compounds which are also selective in gramineous crops, such as rice, corn or wheat, and at the same time control undesirable grasses.

The cyclohexenones of the formula I can be prepared in a conventional manner from known derivatives of the formula II (EP-A 80 301, EP-A 125 094, EP-A 142 741, U.S. Pat. No. 4,249,937, EP-A 137 174 and EP-A 177 913) and the corresponding hydroxylamines of the formula III (Houben-Weyl, 10/1, page 1181 et seq.) (DE-A 34 33 767 and EP-A-48 911).

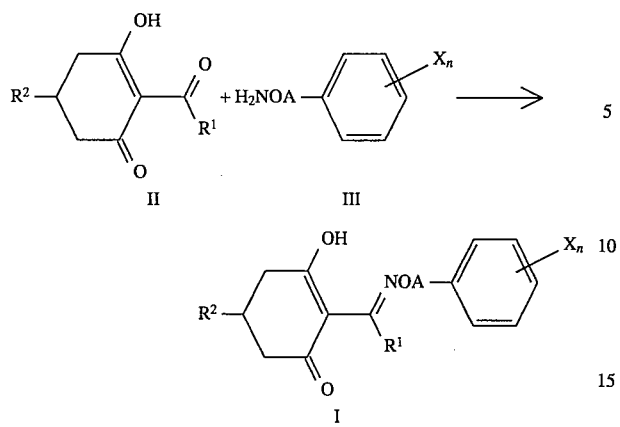

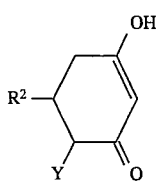

The reaction is advantageously carried out in the heterogeneous phase in a solvent at an adequate temperature below about 80° C., in the presence of a base, and the hydroxylamine III is used in the form of its ammonium salt.

Examples of suitable bases are carbonates, bicarbonates, acetates, alcoholates or oxides of alkali or of alkaline earth metals, in particular sodium hydroxide, potassium hydroxide, magnesium oxide and calcium oxide. Organic bases, such as pyridine or tertiary amines, can also be used. The bases are added, for example in an amount of from 0.5 to 2 mol equivalents, based on the ammonium compound.

Examples of suitable solvents are dimethyl sulfoxide, alcohols, such as methanol, ethanol and isopropanol, aromatic hydrocarbons, such as benzene and toluene, chlorinated hydrocarbons, such as chloroform and dichloroethane, aliphatic hydrocarbons, such as hexane and cyclohexane, esters, such as ethyl acetate, and ethers, such as diethyl ether, dioxane and tetrahydrofuran. The reaction is preferably carried out in methanol, using sodium bicarbonate as the base.

The reaction is complete after a few hours. The desired compound can be isolated, for example, by evaporating down the mixture, partitioning the residue in methylene chloride/water and distilling off the solvent under reduced pressure.

For this reaction, it is however also possible to use the free hydroxylamine base directly, for example in the form of an aqueous solution; a single-phase or two-phase reaction mixture is obtained, depending on the solvent used for compound II.

Suitable solvents for this variant are, for example, alcohols, such as methanol, ethanol, isopropanol and cyclohexanol, aliphatic and aromatic hydrocarbons and chlorohydrocarbons, such as hexane, cyclohexane, methylene chloride, toluene and dichloroethane, esters, such as ethyl acetate, nitriles, such as acetonitrile, and cyclic ethers, such as dioxane and tetrahydrofuran.

Alkali metal salts of the compounds I can be obtained by treating the 3-hydroxy compounds with sodium hydroxide, potassium hydroxide, a sodium alcoholate or a potassium alcoholate in aqueous solution or in an organic solvent, such as methanol, ethanol, acetone or toluene.

Other metal salts, such as manganese, copper, zinc, iron, calcium, magnesium and barium salts, can be prepared from the sodium salts in a conventional manner, as can ammonium and phosphonium salts using ammonia and phosphonium, sulfonium or sulfoxonium hydroxides.

The compounds of type II can be prepared, for example, from the corresponding cyclohexane-1,3-diones of the formula IV where Y is hydrogen or methoxycarbonyl, by known methods (Tetrahedron Lett. (1975), 2491).

It is also possible to prepare the compounds of the formula II via the enol ester intermediates V, which are obtained in the reaction of compounds of the formula IV with acyl chlorides VII in the presence of a base and are then subjected to a rearrangement reaction with certain imidazole or pyridine derivatives (Japanese Preliminary Published Application 79/063 052).

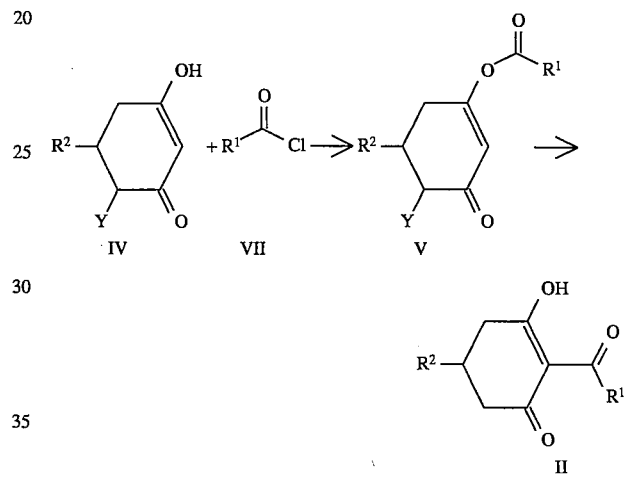

The compounds of the formula IV are obtained via a number of known process steps, starting from known precursors.

The hydroxylamines III

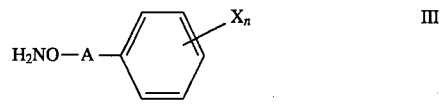

can be prepared by known processes, for example as described in Houben-Weyl, Methoden der organischen Chemie, Vol. 10/1, page 1181 et seq. The procedure described in prior European Application No. 244,786 is particularly preferred when A is an alkenylene chain. This procedure starts from compounds of the formula VI

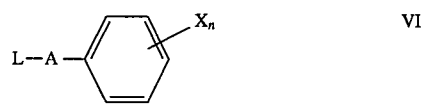

where L is a leaving group which can be displaced under nucleophilic conditions and A is $C_3$-, $C_5$- or $C_6$-alkylene in which the double bond is either in conjugation with the aromatic system or is separated from the latter by 1 or 2 carbon atoms. Particularly suitable substituents of the alkylene group are methyl, chlorine and fluorine. $X_n$ has the meanings stated for the oxime ethers I.

The compounds VI are first reacted with a hydroximide of the formula VIII

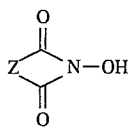
VIII where Z is phenylene, naphthylene, pyridinylene, cyclopentylene, cyclohexylene, cyclohexenylene, $C_2$–$C_4$-alkenylene or $C_1$–$C_4$-alkylene, where these radicals Z are unsubstituted or may carry 1, 2, 3 or 4 halogen, $C_1$–$C_4$-alkyl and/or $C_1$–$C_4$-haloalkyl substituents, in the presence of a solvent and a base at from 0° to 140° C., and the hydroxylamines III are liberated from the resulting imido ethers by means of a base or acid.

If Z is a cyclic, aromatic or heteroaromatic radical, VIII is of course the dicarboximide group of dicarboxylic acids in which the carboxyl groups are in the 1,2-position with respect to one another. Naphthylene is thus

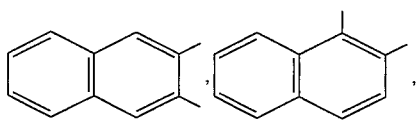

pyridinylene is thus

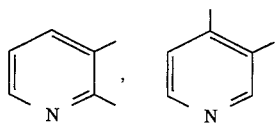

and cyclohexenylene is thus

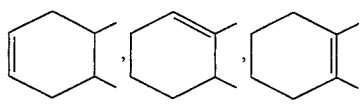

If the radicals Z are substituted, they may have any substitution pattern. However, unsubstituted radicals Z are preferred. The hydroxylamine derivatives in which Z is $C_2$- or $C_3$-alkylene or $C_2$–$C_4$-alkenylene or in particular phenylene are particularly preferred because the starting materials are readily and cheaply available.

Both the hydroxylamine derivatives in which the amino group is protected by a dicarboximide group and the hydroxylamine derivatives containing a free amino group are stable compounds and can be isolated, stored and further processed as such. To isolate the hydroxylamine derivatives having a free amino group, it may, however, be advantageous to convert said derivatives into their salts with organic or inorganic acids, since these salts can more easily be obtained in crystalline form. Moreover, the solubility behavior of these hydroxylammonium salts in organic solvents or water can be influenced in a controlled manner by the choice of the acid anion, a measure which facilitates further processing of the novel hydroxylamine derivatives. The hydroxylammonium salts prepared from the corresponding hydroxylamine derivatives and having anions such as chloride, bromide, sulfate, nitrate, phosphate, formate, acetate, malonate, oxalate, methanesulfonate, benzenesulfonate and toluenesulfonate are particularly preferably used.

The starting compounds VI are known from the literature or can be prepared by processes described there (for example Org. Synth. Coll. Vol. V., 249 and the cited literature, EP 48911, EP 143952 and U.S. Pat. No. 4,686,735). The bromides (VI, L=Br) preferred for the reaction can be synthesized from the corresponding alcohols by general methods (for example Houben-Weyl, Vol. 5/4, page 354 et seq.). For the preparation of the preferred compounds VI in which A is prop-2-enylene, a cinnamic ester or a cinnamaldehyde is reduced (for example Organikum, page 508 et seq.) by conventional methods, and the cinnamyl alcohol thus obtained is converted as described above into the corresponding bromide.

The preparation of the hydroxylamines can be represented by the following reaction scheme:

VI +

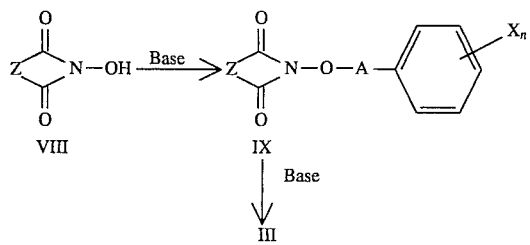

Preferred leaving groups L are the halides chloride, bromide and iodide and the esters of methanesulfonic acid, trifluoromethanesulfonic acid, benzenesulfonic acid, bromobenzenesulfonic acid or toluenesulfonic acid. Particularly preferred leaving groups are the halides chloride and bromide and methanesulfonate and toluenesulfonate.

The reaction of the starting compounds VI with the hydroximides is advantageously carried out in the presence of a base. All bases which are capable of deprotonating the hydroximides VIII without attacking the imide system are in principle suitable. These are, in particular, the non-nucleophilic bases. Examples are mineral bases, such as alkali metal and alkaline earth metal carbonates, alkali metal and alkaline earth metal bicarbonates and organic bases, such as aliphatic, cycloaliphatic and aromatic tertiary amines. Mixtures of these bases can also be used.

Examples of individual compounds are the following bases: sodium carbonate, potassium carbonate, magnesium carbonate, calcium carbonate, barium carbonate, the bicarbonates of these metals, trimethylamine, triethylamine, tributylamine, ethyl diisopropylamine, N,N-dimethylaniline, 4-N,N-dimethylaminopyridine, diazabicyclooctane, diazabicycloundecane, N-methylpiperidine, 1,4-dimethylpiperazine, pyridine, quinoline, bipyridine and phenanthroline. The economical bases sodium carbonate and potassium carbonate are preferred.

The base is generally added in from equivalent amounts to an excess of 5 equivalents, based on the hydroximide. A greater excess is possible but has no additional advantages. The use of a small amount of base is likewise possible. However, the base is preferably used in an amount of from 1 to 3, in particular from 1 to 2, equivalents, based on the hydroximide VIII.

The use of nucleophilic bases, for example alkali metal and alkaline earth metal hydroxides, in particular sodium hydroxide and potassium hydroxide is also possible. In this case, it is advantageous to use the base in equivalent amounts, based on the hydroximide VI, in order to prevent nucleophilic attack by the hydroxyl ions on the carbonyl function of the imide group.

The starting compounds VI are advantageously reacted with the hydroximides VIII in a solvent which is inert under the reaction conditions. Advantageous solvents are, for example, polar aprotic solvents, such as dimethylformamide, N-methylpyrrolidone, dimethyl sulfoxide, sulfolane and cyclic ureas. The amount of solvent is in general not critical.

The reaction of the starting compounds VI with the hydroximides VIII can also be carried out using phase transfer catalysis. In this case, solvents, preferably chlorohydrocarbons, which form two phases with water are used. Suitable phase transfer catalysts are the quaternary ammonium and phosphonium salts, polyethylene glycols, polyethylene glycol ethers and crown ethers which are usually used for such purposes and are described in, for example, Dehmlow et al., Phase Transfer Catalysis, pages 37–45 and pages 86–93, Verlag Chemie, Weinheim 1980. The phase transfer catalysts are advantageously used in amounts of from 1 to 10, preferably from 3 to 5, % by volume, based on the volume of the reaction mixture.

The reaction of the starting compounds VI with the hydroximides VIII is carried out in general at from 0° to 140° C., preferably from 20° to 100° C., in particular from 40° to 80° C. In an advantageous procedure, the hydroximide VIII is initially taken together with the base in the solvent, and the starting material VI is metered into the solution. It may prove advantageous if the hydroximide is added at a lower temperature, for example at from 0° to 50° C., and the reaction mixture is not heated to the actual reaction temperature until this addition is complete.

After the end of the reaction, water is advantageously added to the cooled reaction mixture, the resulting hydroxylamine derivatives IX separating out as crystalline solids or as oils. The hydroxylamine derivatives obtained in this manner can, if desired, be further purified by recrystallization or by extraction.

The hydroxylamine derivatives IX are temporarily stored or are immediately converted into the hydroxylamine derivatives having a free amino group. This conversion can be carried out by conventional processes, as described, for example, in DE-A 36 15 973 and the publications cited therein. The process according to DE-A 36 15 973 is preferably used, in which the hydroxylamine derivatives III are liberated by means of ethanolamine. Liberation of the hydroxylamine derivatives III with the aid of other bases, such as aqueous mineral bases, with amines, hydrazines or hydroxylamines or by means of aqueous acids, is also possible.

The hydroxylamine derivatives III can be isolated from the reaction mixtures obtained in these processes by means of conventional working up methods, for example by extraction or by crystallization. To increase the tendency of these hydroxylamine derivatives to crystallize, it may often be necessary to convert said derivatives into their salts with mineral acids or organic acids. Dilute solutions of these acids are generally reacted with the hydroxylamine derivatives for this purpose, advantageously in equivalent amounts. The resulting hydroxylammonium salts can, like the hydroxylamine derivatives having a free amino group, be further processed directly to the herbicides of the formula I or, if desired, stored.

Preferred cyclohexenones of the formula I are those in which the substituents have the following meanings:

$R^1$ is alkyl, such as methyl, isopropyl, n-butyl, isobutyl or tert-butyl, in particular ethyl or n-proyl;

A is propylene, prop-2-enylene, pentylene, pent-2-enylene, pent-3-enylene, pent-4-enylene, hexylene, hex-2-enylene, hex-3-enylene, hex-4-enylene or hex-5-enylene, each of which is unsubstituted or substituted by up to 3 methyl radicals or one methylene radical and/or fluorine or chlorine; in the case of the unsaturated chains, both the cis and the trans form may occur; prop-2-enylene is particularly preferred;

X is halogen, such as fluorine, chlorine, bromine or iodine, in particular fluorine or chlorine, alkyl, such as methyl, ethyl, propyl, 1-methylethyl, butyl, 1-methylpropyl, 2-methylpropyl or 1,1-dimethylethyl, in particular methyl, alkoxy, such as methoxy, ethoxy, propoxy, 1-methylethoxy, butoxy, 1-methylpropoxy, 2-methylpropoxy or 1,1-dimethylethoxy, in particular methoxy, ethoxy, 1-methylethoxy or 1,1-dimethylethoxy, alkylthio, such as methylthio, ethylthio, propylthio, 1-methylethylthio, butylthio, 1-methylpropylthio, 2-methylpropylthio or 1,1-dimethylethylthio, in particular methylthio or ethylthio, haloalkyl, such as fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro-2,2-difluoroethyl, 2,2-dichloro-2-fluoroethyl, 2,2,2-trichloroethyl or pentafluoroethyl, in particular difluoromethyl, trifluoromethyl, 2,2,2-trifluoroethyl or pentafluoroethyl, haloalkoxy, such as difluoromethoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy or pentafluoroethoxy, in particular trifluoromethoxy, alkoxycarbonyl, such as methoxycarbonyl, ethoxycarbonyl, propoxycarbonyl, 1-methylethoxycarbonyl, butoxycarbonyl or 1,1-dimethylethoxycarbonyl, in particular methoxycarbonyl, ethoxycarbonyl or 1,1-dimethylethoxycarbonyl, especially methoxycarbonyl, or hydrogen, nitro, cyano, benzyloxycarbonyl, phenoxy or phenyl, where the aromatic radicals may be substituted.

Particularly suitable substituents here are nitro, cyano, carboxyl, benzyloxycarbonyl and the above-mentioned halogen atoms, alkyl, alkoxy, alkylthio, haloalkyl, haloalkoxy and/or alkoxycarbonyl groups. Unsubstituted or monosubstituted aromatic radicals of this type are particularly preferred.

n is 0, 1, 2 or 3, in particular 0, 1 or 2. Where there is a plurality of radicals X, the substituents may be identical or different.

$R^2$ is alkyl as stated under $R^1$, which may carry, preferably in the 1-, 2- or 3-position, one of the alkoxy or alkylthio groups stated under X, in particular 2-ethylthiopropyl, 5-membered heterocycloalkyl, such as tetrahydrofuranyl, tetrahydrothienyl, dioxolanyl, dithiolanyl or oxathiolanyl, in particular tetrahydrofuranyl or dioxolanyl, where these rings may carry from one to three of the $C_1$–$C_4$-alkyl, $C_1$–$C_4$-alkoxy, $C_1$–$C_4$-alkylthio and/or $C_1$–$C_4$-haloalkyl groups stated above under X, 5-membered hetaryl, such as pyrrolyl, pyrazolyl, imidazolyl, isoxazolyl, oxazolyl, isothiazolyl, thiazolyl, furanyl or thienyl, in particular isoxazolyl or furanyl, a 6-membered or 7-membered heterocyclic structure, such as tetrahydropyran-3-yl, dihydropyran-3-yl, tetrahydropyran-4-yl, dihydropyran-4-yl, tetrahydrothiopyran-3-yl, dihydrothiopyran-3-yl, tetrahydrothiopyran-4-yl, dihydrothiopyran-4-yl or dioxepan-5-yl, in particular tetrahydropyran-3-yl, tetrahydropyran-4-yl or tetrahydrothiopyran-3-yl, phenyl or pyridyl, where the cyclic radicals may carry from one to three of the alkyl, alkoxy, alkylthio and/or haloalkyl groups stated under X.

The 5-membered heteroaromatic structures $R^2$ may carry the following radicals as substituents: halogen as stated under X, in particular fluorine or chlorine, alkoxyalkyl, such as methoxymethyl, 2-methoxyethyl, 2-methoxypropyl, 3-methoxypropyl, 2-methoxy-1-methylethyl, ethoxymethyl, 2-ethoxyethyl, 2-ethoxypropyl, 3-ethoxypropyl, 2-ethoxy-1-methylethyl or 1-ethoxy-1-methylethyl, in particular methoxyethyl or ethoxyethyl, alkenyl, such as ethenyl, 1-propenyl, 2-propenyl, 1-methylethenyl, 1-butenyl, 2-butenyl, 3-butenyl, 1-methyl-1-propenyl, 1-methyl-2-propenyl, 2-methyl-1-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl or 1-ethyl-2-methyl-2-propenyl, in particular 1-methylethenyl, or corresponding alkenyloxy and/or haloalkenyl radicals.

The 6-membered and 7-membered heterocyclic structures may also carry hydroxyl groups in addition to the above-mentioned substituents.

In the phenyl and pyridyl radicals, suitable substituents in addition to the above-mentioned groups are cyano, nitro and amino, and the amino groups may be unsubstituted or monosubstituted or disubstituted by the stated alkyl and/or alkenyl groups. Other suitable substitutents on amino groups are the following radicals: alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-3-butynyl, 2-methyl-3-butynyl, 1-methyl-2-butynyl, 3-methyl-1-butynyl, 1,1-dimethyl-2-propynyl, 1-ethyl-2-propynyl, 1-hexynyl, 2-hexynyl, 3-hexynyl, 4-alkynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl or 1-ethyl-1-methyl-2-propynyl, in particular 2-propynyl or 2-butynyl and/or acyl, such as acetyl, propionyl, butyryl, 2-methylpropionyl, pentanoyl, 2-methylbutyryl, 3-methylbutyryl, 2,2-dimethylpropionyl, hexanoyl, 2-methylpentanoyl, 3-methylpentanoyl, 4-methylpentanoyl, 2,2-dimethylbutyryl, 2,3-dimethylbutyryl, 3,3-dimethylbutyryl or 2-ethylbutyryl, in particular acetyl or propionyl, or benzoyl.

Suitable salts of the compounds of the formula I are agriculturally useful salts, for example alkali metal salts, such as the potassium or sodium salt, alkaline earth metal salts, such as the calcium, magnesium or barium salt, or manganese, copper, zinc and iron salts and ammonium, phosphonium, sulfonium and sulfoxonium salts, for example ammonium salts, tetraalkylammonium salts, benzyltrialkylammonium salts, trialkylsulfonium salts and trialkylsulfoxonium salts.

With regard to the biological activity, specific examples of these cyclohexenone oxime ethers are summarized in the Tables below.

TABLE A

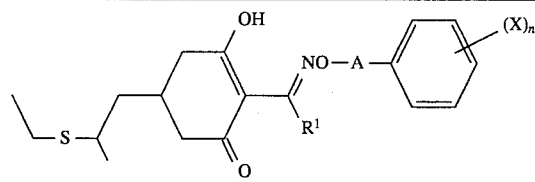

| $R^1$ | A | X | n |
|---|---|---|---|
| $CH_2CH_3$ | $(CH_2)_5$ | — | 0 |
| $(CH_2)_2CH_3$ | $CH_2CH=CH$ | — | 0 |
| $CH_2CH_3$ | $(CH_2)_3CH=CH$ | — | 0 |
| $(CH_2)_2CH_3$ | $(CH_2)_4CH=CH$ | — | 0 |
| $CH_2CH_3$ | $(CH_2)CH=CH$ | 4-$CF_3$ | 1 |
| $(CH_2)_2CH_3$ | $(CH_2)CH=CH$ | 4-$CF_3$ | 1 |
| $CH_2CH_3$ | $(CH_2)CH=CH$ | 3-F | 1 |
| $(CH_2)_2CH_3$ | $(CH_2)CH=CH$ | 3-F | 1 |
| $CH_2CH_3$ | $(CH_2)CH=CH$ | 4-F | 1 |
| $(CH_2)_2CH_3$ | $(CH_2)CH=CH$ | 4-F | 1 |
| $CH_2CH_3$ | $(CH_2)CH=CH$ | 3-$CH_3$ | 1 |
| $(CH_2)_2CH_3$ | $(CH_2)CH=CH$ | 3-$CH_3$ | 1 |
| $CH_2CH_3$ | $(CH_2)CH=CH$ | 4-$OCH_3$ | 1 |
| $(CH_2)_2CH_3$ | $(CH_2)CH=CH$ | 4-$OCH_3$ | 1 |
| $CH_2CH_3$ | $(CH_2)CH=CH$ | 3-$NO_2$ | 1 |
| $(CH_2)_2CH_3$ | $(CH_2)CH=CH$ | 3-$NO_2$ | 1 |
| $CH_2CH_3$ | $(CH_2)CH=CH$ | 3-CN | 1 |
| $(CH_2)_2CH_3$ | $(CH_2)CH=CH$ | 3-CN | 1 |
| $CH_2CH_3$ | $(CH_2)CH=CH$ | 3-$CO_2CH_3$ | 1 |
| $(CH_2)_2CH_3$ | $(CH_2)CH=CH$ | 3-$CO_2CH_3$ | 1 |
| $CH_2CH_3$ | $(CH_2)CH=CH$ | 3-$CO_2Ph$ | 1 |
| $(CH_2)_2CH_3$ | $(CH_2)CH=CH$ | 3-$CO_2Ph$ | 1 |
| $CH_2CH_3$ | $(CH_2)CH=CH$ | 4-$OCHF_2$ | 1 |
| $(CH_2)_2CH_3$ | $(CH_2)CH=CH$ | 4-$OCHF_2$ | 1 |
| $CH_2CH_3$ | $(CH_2)CH=CH$ | 3-$CH_3$,4-Cl | 1 |
| $(CH_2)_2CH_3$ | $(CH_2)CH=CH$ | 3-$CH_3$,4-Cl | 1 |
| $CH_2CH_3$ | $CH_2CH=CH$ | 4-Cl | 1 |
| $(CH_2)_2CH_3$ | $CH_2CH=CH$ | 4-Cl | 1 |
| $CH_2CH_3$ | $(CH_2)_2CH=CH-CH_2$ | 4-Cl | 1 |
| $CH_2CH_3$ | $CH_2CH=CH-(CH_2)_2$ | 4-Cl | 1 |
| $CH_2CH_3$ | $CH_2CH=CH$ | 4-CN | 1 |
| $CH_2CH_3$ | $(CH_2)_4CH=CH$ | 2,4-$Cl_2$ | 1 |

TABLE B

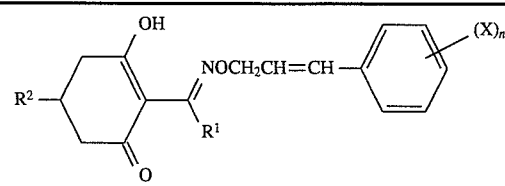

| $R^1$ | $R^2$ | X | n |
|---|---|---|---|
| $CH_2CH_3$ | (cyclopentyl-O) | — | 0 |
| $(CH_2)_2CH_3$ | (cyclopentyl-O) | — | 0 |

TABLE B-continued

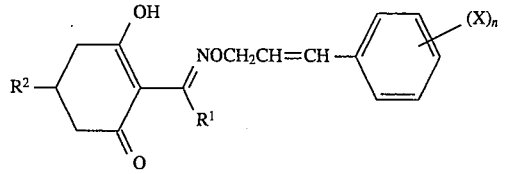

| R¹ | R² | X | n |
|---|---|---|---|
| CH₂CH₃ | 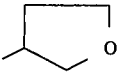 | 4-F | 1 |
| (CH₂)₂CH₃ | 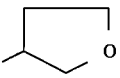 | 4-F | 1 |
| CH₂CH₃ |  | 3-CH₃ | 1 |
| (CH₂)₂CH₃ |  | 3-CH₃ | 1 |
| CH₂CH₃ | 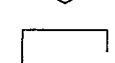 | 3-CF₃ | 1 |
| (CH₂)₂CH₃ | 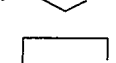 | 3-CF₃ | 1 |
| CH₂CH₃ | 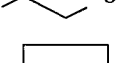 | 4-C(CH₃)₃ | 1 |
| (CH₂)₂CH₃ | 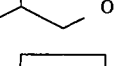 | 4-C(CH₃)₃ | 1 |
| CH₂CH₃ | 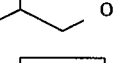 | 3-Cl | 1 |
| (CH₂)₂CH₃ | 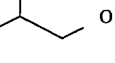 | 3-Cl | 1 |
| CH₂CH₃ | 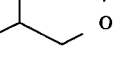 | — | 0 |
| (CH₂)₂CH₃ | 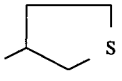 | — | 0 |
| CH₂CH₃ | 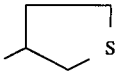 | 4-F | 1 |
| (CH₂)₂CH₃ | 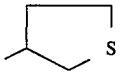 | 4-F | 1 |
| CH₂CH₃ |  | 3-CH₃ | 1 |
| (CH₂)₂CH₃ |  | 3-CH₃ | 1 |

TABLE B-continued

| R¹ | R² | X | n |
|---|---|---|---|
| CH₂CH₃ |  | 3-CF₃ | 1 |
| (CH₂)₂CH₃ | 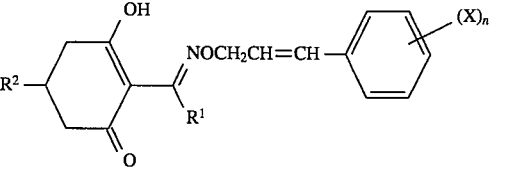 | 3-CF₃ | 1 |
| CH₂CH₃ |  | 4-C(CH₃)₃ | 1 |
| (CH₂)₂CH₃ |  | 4-C(CH₃)₃ | 1 |
| CH₂CH₃ |  | 3-Cl | 1 |
| (CH₂)₂CH₃ | 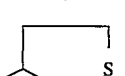 | 3-Cl | 1 |
| CH₂CH₃ | 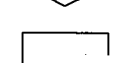 | — | 0 |
| (CH₂)₂CH₃ | 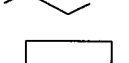 | — | 0 |
| CH₂CH₃ | 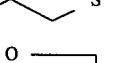 | 4-F | 1 |
| (CH₂)₂CH₃ | 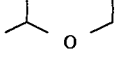 | 4-F | 1 |
| CH₂CH₃ | 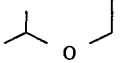 | 3-CH₃ | 1 |
| (CH₂)₂CH₃ | 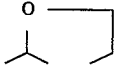 | 3-CH₃ | 1 |
| CH₂CH₃ |  | 3-CF₃ | 1 |
| (CH₂)₂CH₃ | 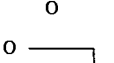 | 3-CF₃ | 1 |
| CH₂CH₃ | 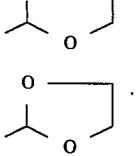 | 4-C(CH₃)₃ | 1 |

TABLE B-continued
| | OH NOCH₂CH=CH—phenyl(X)ₙ cyclohexanone with R² and R¹ | | | |
|---|---|---|---|---|
| R¹ | R² | X | n | |
| R¹ | R² | X | n |
|---|---|---|---|
| (CH₂)₂CH₃ | 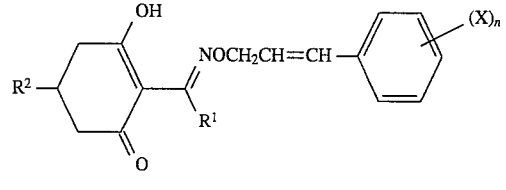 | 4-C(CH₃)₃ | 1 |
| CH₂CH₃ | 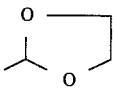 | 3-Cl | 1 |
| (CH₂)₂CH₃ | 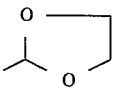 | 3-Cl | 1 |
| CH₂CH₃ | 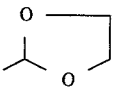 | — | 0 |
| (CH₂)₂CH₃ | 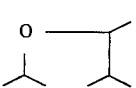 | — | 0 |
| CH₂CH₃ | 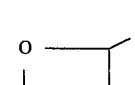 | 4-F | 1 |
| (CH₂)₂CH₃ | 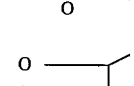 | 4-F | 1 |
| CH₂CH₃ | 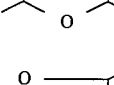 | 3-CH₃ | 1 |
| (CH₂)₂CH₃ | 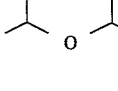 | 3-CH₃ | 1 |
| CH₂CH₃ | 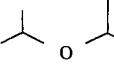 | 3-CF₃ | 1 |
| (CH₂)₂CH₃ | 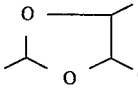 | 3-CF₃ | 1 |
| CH₂CH₃ | 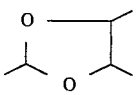 | 4-C(CH₃)₃ | 1 |
| (CH₂)₂CH₃ | 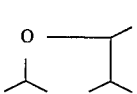 | 4-C(CH₃)₃ | 1 |
| CH₂CH₃ | 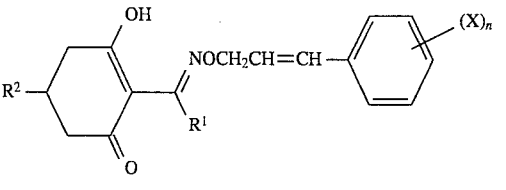 | 3-Cl | 1 |
| (CH₂)₂CH₃ | 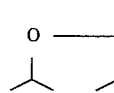 | 3-Cl | 1 |
| CH₂CH₃ | 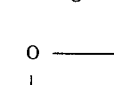 | — | 0 |
| (CH₂)₂CH₃ | 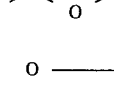 | — | 0 |
| CH₂CH₃ | 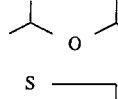 | 4-F | 1 |
| (CH₂)₂CH₃ | 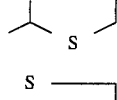 | 4-F | 1 |
| CH₂CH₃ | 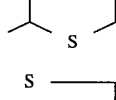 | 3-CH₃ | 1 |
| (CH₂)₂CH₃ | 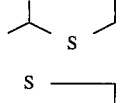 | 3-CH₃ | 1 |
| CH₂CH₃ | 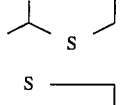 | 3-CF₃ | 1 |
| (CH₂)₂CH₃ | 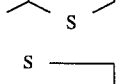 | 3-CF₃ | 1 |
| CH₂CH₃ | 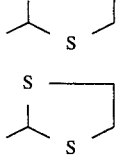 | 4-C(CH₃)₃ | 1 |

TABLE B-continued

![structure](OH, R², R¹, NOCH₂CH=CH-phenyl-(X)ₙ, cyclohexenone)

| R¹ | R² | X | n |
|---|---|---|---|
| (CH₂)₂CH₃ | S-CH(iPr)-S (dithiane) | 4-C(CH₃)₃ | 1 |
| CH₂CH₃ | S-CH(iPr)-S (dithiane) | 3-Cl | 1 |
| (CH₂)₂CH₃ | S-CH(iPr)-S (dithiane) | 3-Cl | 1 |
| CH₂CH₃ | tetrahydropyranyl (O) | — | 0 |
| (CH₂)₂CH₃ | tetrahydropyranyl (O) | — | 0 |
| CH₂CH₃ | tetrahydropyranyl (O) | 4-F | 1 |
| (CH₂)₂CH₃ | tetrahydropyranyl (O) | 4-F | 1 |
| CH₂CH₃ | tetrahydropyranyl (O) | 3-CH₃ | 1 |
| (CH₂)₂CH₃ | tetrahydropyranyl (O) | 3-CH₃ | 1 |
| CH₂CH₃ | tetrahydropyranyl (O) | 3-CF₃ | 1 |
| (CH₂)₂CH₃ | tetrahydropyranyl (O) | 3-CF₃ | 1 |
| CH₂CH₃ | tetrahydropyranyl (O) | 4-C(CH₃)₃ | 1 |
| (CH₂)₂CH₃ | tetrahydropyranyl (O) | 4-C(CH₃)₃ | 1 |
| CH₂CH₃ | tetrahydropyranyl (O) | 3-Cl | 1 |
| (CH₂)₂CH₃ | tetrahydropyranyl (O) | 3-Cl | 1 |
| CH₂CH₃ | Br,Br-tetrahydropyranyl (O) | — | 0 |
| (CH₂)₂CH₃ | Br,Br-tetrahydropyranyl (O) | — | 0 |
| CH₂CH₃ | Br,Br-tetrahydropyranyl (O) | 4-F | 1 |
| (CH₂)₂CH₃ | Br,Br-tetrahydropyranyl (O) | 4-F | 1 |
| CH₂CH₃ | Br,Br-tetrahydropyranyl (O) | 3-CH₃ | 1 |
| (CH₂)₂CH₃ | Br,Br-tetrahydropyranyl (O) | 3-CH₃ | 1 |
| CH₂CH₃ | Br,Br-tetrahydropyranyl (O) | 3-CF₃ | 1 |

TABLE B-continued

Structure: cyclohexenone with OH, R², and C(R¹)=NOCH₂CH=CH-phenyl-(X)ₙ substituents

| R¹ | R² | X | n |
|---|---|---|---|
| (CH₂)₂CH₃ | 3,4-dibromotetrahydropyran-4-yl | 3-CF₃ | 1 |
| CH₂CH₃ | 3,4-dibromotetrahydropyran-4-yl | 4-C(CH₃)₃ | 1 |
| (CH₂)₂CH₃ | 3,4-dibromotetrahydropyran-4-yl | 4-C(CH₃)₃ | 1 |
| CH₂CH₃ | 3,4-dibromotetrahydropyran-4-yl | 3-Cl | 1 |
| (CH₂)₂CH₃ | 3,4-dibromotetrahydropyran-4-yl | 3-Cl | 1 |
| CH₂CH₃ | 2-methyl-isothiazol-5-yl | — | 0 |
| (CH₂)₂CH₃ | 2-methyl-isothiazol-5-yl | — | 0 |
| CH₂CH₃ | 2-methyl-isothiazol-5-yl | 4-F | 1 |
| (CH₂)₂CH₃ | 2-methyl-isothiazol-5-yl | 4-F | 1 |
| CH₂CH₃ | 2-methyl-isothiazol-5-yl | 3-CH₃ | 1 |
| (CH₂)₂CH₃ | 2-methyl-isothiazol-5-yl | 3-CH₃ | 1 |
| CH₂CH₃ | 2-methyl-isothiazol-5-yl | 3-CF₃ | 1 |
| (CH₂)₂CH₃ | 2-methyl-isothiazol-5-yl | 3-CF₃ | 1 |
| CH₂CH₃ | 2-methyl-isothiazol-5-yl | 4-C(CH₃)₃ | 1 |
| (CH₂)₂CH₃ | 2-methyl-isothiazol-5-yl | 4-C(CH₃)₃ | 1 |
| CH₂CH₃ | 2-methyl-isothiazol-5-yl | 3-Cl | 1 |
| (CH₂)₂CH₃ | 2-methyl-isothiazol-5-yl | 3-Cl | 1 |
| CH₂CH₃ | 2-isobutyl-2-(1,1-dimethyl)-1,3-dioxolane | 3-CF₃ | 1 |
| (CH₂)₂CH₃ | 2-isobutyl-2-(1,1-dimethyl)-1,3-dioxolane | 3-CF₃ | 1 |
| CH₂CH₃ | 2-isobutyl-2-(1,1-dimethyl)-1,3-dioxolane | 4-C(CH₃)₃ | 1 |
| (CH₂)₂CH₃ | 2-isobutyl-2-(1,1-dimethyl)-1,3-dioxolane | 4-C(CH₃)₃ | 1 |
| CH₂CH₃ | 2-isobutyl-2-(1,1-dimethyl)-1,3-dioxolane | — | 0 |
| (CH₂)₂CH₃ | 2-isobutyl-2-(1,1-dimethyl)-1,3-dioxolane | — | 0 |
| CH₂CH₃ | 2-isobutyl-1,3-dioxolane | — | 0 |
| (CH₂)₂CH₃ | 2-isobutyl-1,3-dioxolane | — | 0 |
| CH₂CH₃ | 2-isobutyl-1,3-dioxolane | 3-CF₃ | 1 |

TABLE B-continued

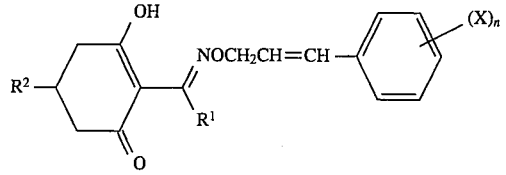

| R¹ | R² | X | n |
|---|---|---|---|
| (CH₂)₂CH₃ | 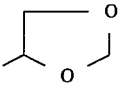 | 3-CF₃ | 1 |
| CH₂CH₃ | 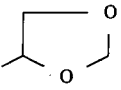 | 4-C(CH₃)₃ | 1 |
| (CH₂)₂CH₃ | 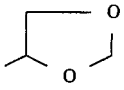 | 4-C(CH₃)₃ | 1 |
| CH₂CH₃ |  | — | 0 |
| (CH₂)₂CH₃ |  | — | 0 |
| CH₂CH₃ | 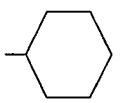 | 3-CF₃ | 1 |
| (CH₂)₂CH₃ | 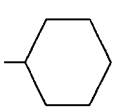 | 3-CF₃ | 1 |
| CH₂CH₃ | 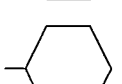 | 4-C(CH₃)₃ | 1 |
| (CH₂)₂CH₃ | 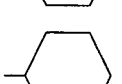 | 4-C(CH₃)₃ | 1 |
| CH₂CH₃ | 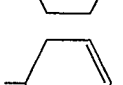 | — | 0 |
| (CH₂)₂CH₃ | 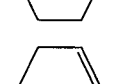 | — | 0 |
| CH₂CH₃ | 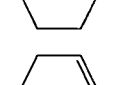 | 3-CF₃ | 1 |
| (CH₂)₂CH₃ | 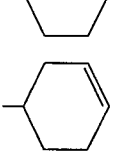 | 3-CF₃ | 1 |

TABLE B-continued

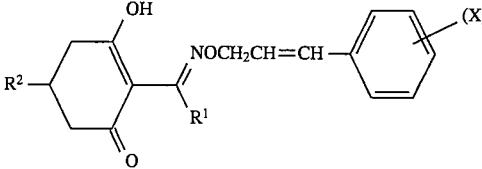

| R¹ | R² | X | n |
|---|---|---|---|
| CH₂CH₃ |  | 4-C(CH₃)₃ | 1 |
| (CH₂)₂CH₃ | 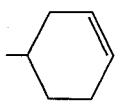 | 4-C(CH₃)₃ | 1 |

The cyclohexenone oxime ethers I or the herbicides containing them can be applied, for example, in the form of directly sprayable solutions, powders, suspensions, including concentrated aqueous, oily or other suspensions or dispersions, emulsions, oil dispersions, pastes, dusting agents, broadcasting agents, or granules, by spraying, atomizing, dusting, broadcasting or pouring. The application forms depend on the intended uses; they should in any case ensure very fine distribution of the novel active ingredients.

The compounds I are suitable in general for the preparation of directly sprayable solutions, emulsions, pastes or oil dispersions. Suitable inert additives are mineral oil fractions having a medium to high boiling point, such as kerosene or diesel oil, as well as coal tar oils and oils of vegetable or animal origin, aliphatic, cyclic and aromatic hydrocarbons, eg. toluene, xylene, paraffin, tetrahydronaphthalene, alkylated naphthalenes or their derivatives, methanol, ethanol, propanol, butanol, cyclohexanol, cyclohexanone, chlorobenzene, isophorone or strongly polar solvents, such as N,N-dimethylformamide, dimethyl sulfoxide, N-methylpyrrolidone or water.

Aqueous application forms can be prepared from emulsion concentrates, dispersions, pastes, wettable powders or water-dispersible granules by adding water. To prepare emulsions, pastes or oil dispersions, the substrates, as such or dissolved in an oil or solvent, can be homogenized in water by means of wetting agents, adherents, dispersants or emulsifiers. However, it is also possible to prepare concentrates which consist of active substance, wetting agents, adherents, dispersants or emulsifiers and possibly solvents or oil and which are suitable for dilution with water.

Suitable surfactants are the alkali metal, alkaline earth metal and ammonium salts of aromatic sulfonic acids, for example lignin-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and also salts of sulfated hexa-, hepta- and octa-decanols, and of fatty alcohol glycol ethers, condensates of sulfonated naphthalene and its derivatives with formaldehyde, condensates of naphthalene or of naphthalenesulfonic acids with phenol and formaldehyde, polyoxyethylene octylphenol ethers, ethoxylated isooctyl-, octyl- or nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene, lauryl alcohol polyglycol ether acetate, sorbitol esters, lignin sulfite waste liquors or methyl cellulose.

Powders, broadcasting agents and dusting agents can be prepared by mixing or milling the active substances together with a solid carrier.

Granules, for example coating, impregnated and homogeneous granules, can be prepared by binding the active ingredients to solid carriers. Solid carriers are mineral earths, such as silica gel, silicas, silicates, talc, kaolin, limestone, lime, chalk, bole, loess, clay, dolomite, kieselguhr, calcium sulfate, magnesium sulfate, magnesium oxide, milled plastics, fertilizers, such as ammonium sulfate, ammonium phosphate, ammonium nitrate or ureas, and vegetable products, such as grain flours, bark meal, wood meal and nutshell meal, cellulosic powders and other solid carriers.

The formulations contain in general from 0.02 to 95, preferably from 0.5 to 90, % by weight of active ingredient. The active ingredients are used in a purity of from 90 to 100%, preferably from 95 to 100% (according to NMR/HPLC/GC spectrum).

Examples of such formulations are:

I. a solution of 90 parts by weight of compound 1.1 and 10 parts by weight of N-methyl-α-pyrrolidone, which solution is suitable for use in the form of very small drops;

II. a mixture of 20 parts by weight of compound 1.2, 80 parts by weight of xylene, 10 parts by weight of the adduct of from 8 to 10 mol of ethylene oxide with 1 mol of N-monoethanolamide, 5 parts by weight of the calcium salt of dodecylbenzenesulfonic acid, and 5 parts by weight of the adduct of 40 mol of ethylene oxide with 1 mol of castor oil. By finely distributing the mixture in 100,000 parts by weight of water, a dispersion which contains 0.02% by weight of the active ingredient is obtained.

III. an aqueous dispersion of 20 parts by weight of compound 1.4, 40 parts by weight of cyclohexanone, 30 parts by weight of isobutanol and 20 parts by weight of the adduct of 40 mol of ethylene oxide with 1 mol of castor oil. A mixture of this dispersion with 100,000 parts by weight of water contains 0.02% by weight of the active ingredient.

IV. an aqueous dispersion of 20 parts by weight of compound 1.17, 25 parts by weight of cyclohexanol, 65 parts by weight of a mineral oil fraction boiling within a range of from 210° to 280° C. and 10 parts by weight of the adduct of 40 mol of ethylene oxide with 1 mol of castor oil. A mixture of this dispersion with 100,000 parts by weight of water contains 0.02% of the active ingredient.

V. a mixture, milled in a hammer mill, of 80 parts by weight of compound 2.2, 3 parts by weight of the sodium salt of diisobutylnaphthalene-α-sulfonic acid, 10 parts by weight of the sodium salt of a ligninsulfonic acid obtained from a sulfite waste liquor and 7 parts by weight of silica gel powder. By finely distributing the mixture in 20,000 parts by weight of water, a spray liquor which contains 0.1% by weight of the active ingredient is obtained.

VI. a thorough mixture of 3 parts by weight of compound 2.4 and 97 parts by weight of finely divided kaolin. This dusting agent contains 3% by weight of the active ingredient.

VII. a thorough mixture of 30 parts by weight of compound 2.7, 92 parts by weight of silica gel powder and 8 parts by weight of liquid paraffin, which has been sprayed onto the surface of the silica gel. This formulation imparts good adhesion to the active ingredient.

VIII. a stable aqueous dispersion of 40 parts by weight of compound 3.1, 10 parts by weight of the sodium salt of a phenolsulfonic acid/urea/formaldehyde condensate, 2 parts by weight of silica gel and 48 parts by weight of water, which can be further diluted.

IX. a stable oily dispersion of 20 parts by weight of compound 4.1, 2 parts by weight of the calcium salt of dodecylbenzenesulfonic acid, 8 parts by weight of a fatty alcohol polyglycol ether, 20 parts by weight of the sodium salt of a phenolsulfonic acid/urea/formaldehyde condensate and 68 parts by weight of a paraffinic mineral oil.

X. a mixture, milled in a hammer mill, of 10 parts by weight of compound 3.17, 4 parts by weight of the sodium salt of diisobutylnaphthalene-α-sulfonic acid, 20 parts by weight of the sodium salt of a ligninsulfonic acid obtained from a sulfite waste liquor, 38 parts by weight of silica gel and 38 parts by weight of kaolin. By finely distributing the mixture in 10,000 parts by weight of water, a spray liquor which contains 0.1% by weight of the active ingredient is obtained.

The herbicides or the active ingredients can be applied by the pre-emergence or post-emergence method. If the active ingredients are less well tolerated by certain crops, it is possible to use application methods in which the herbicides are sprayed with the aid of sprayers in such a way that the leaves of the sensitive crops are, as far as possible, not affected, whereas the active ingredients reach the leaves of undesirable plants growing underneath or the exposed soil surface (post-directed, lay-by).

The application rates of active ingredient are from 0,001 to 3.0, preferably from 0.01 to 2.0, kg/ha of active substance (a.s.), depending on the aim of control, the season, the target plants and the stage of growth.

In view of the wide range of application methods, the novel compounds or agents containing them can be used in a further number of crops for eliminating undesirable plants. Examples of suitable crops are the following:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Beta vulgaris spp. altissima | sugarbeets |
| Beta vulgaris spp. rapa | fodder beets |
| Brassica napus var. napus | rapeseed |
| Brassica napus var. napobrassica | swedes |
| Brassica rapa var. silvestris | beets |
| Camellia sinensis | tea plants |
| Carthamus tinctorius | safflower |
| Carya illinoinensis | pecan trees |
| Citrus limon | lemons |
| Citrus sinensis | orange trees |
| Coffea arabica (Coffea canephora, Coffea liberica) | coffee plants |
| Cucumis sativus | cucumbers |
| Cynodon dactylon | Bermudagrass in turf and lawns |
| Daucus carota | carrots |
| Elaeis guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Hordeum vulgare | barley |
| Humulus lupulus | hops |
| Ipomoea batatas | sweet potatoes |
| Juglans regia | walnut trees |
| Lens culinaris | lentils |
| Linum usitatissimum | flax |
| Lycopersicon lycopersicum | tomatoes |

| Botanical name | Common name |
|---|---|
| Malus spp. | apple trees |
| Manihot esculenta | cassava |
| Medicago sativa | alfalfa (lucerne) |
| Musa spp. | banana plants |
| Nicotiana tabacum (N. rustica) | tobacco |
| Olea europaea | olive trees |
| Oryza sativa | rice |
| Phaseolus lunatus | limabeans |
| Phaseolus vulgaris | snapbeans, green beans, dry beans |
| Picea abies | Norway spruce |
| Pinus spp. | pine trees |
| Pisum sativum | English peas |
| Prunus avium | cherry trees |
| Prunue persica | peach trees |
| Pyrus communis | pear trees |
| Ribes sylvestre | redcurrants |
| Ricinus communis | castor-oil plants |
| Saccharum officinarum | sugar cane |
| Secale cereale | rye |
| Solanum tuberosum | Irish potatoes |
| Sorghum bicolor (s. vulgare) | sorghum |
| Theobroma cacao | cacao plants |
| Trifolium pratense | red clover |
| Triticum aestivum | wheat |
| Triticum durum | durum wheat |
| Vicia faba | tick beans |
| Vitis vinifera | grapes |
| Zea mays | Indian corn, sweet corn, maize |

To extend the action spectrum and to achieve synergistic effects, the novel compounds I can be mixed and applied together with a large number of members of other groups of herbicidal or growth-regulating acting ingredients. Examples of suitable components for the mixture are diazines, 4H-3,1-benzoxazine derivatives, benzothiadiazinones, 2,6-dinitroanilines, N-phenylcarbamates, thiocarbamates, halocarboxylic acids, triazines, aides, ureas, diphenyl ethers, triazinones, uracils, benzofuran derivatives, cyclohexane-1, 3-dione derivatives, quinolinecarboxylic acid derivatives, aryloxy- and hetaryloxyphenoxypropionic acids and their salts, esters and amides, etc.

It may also be advantageous to apply the compounds I, alone or in combination with other herbicides, as a mixture with other crop protection agents, for example with pesticides or agents for controlling phyto-pathogenic fungi or bacteria. The miscibility with mineral salt solutions used for eliminating nutrient and trace element deficiencies is also of interest. It is also possible to add nonphytotoxic oils and oil concentrates.

The method described in Synthesis Example I below was used for obtaining further compounds of the formula I, with appropriate modification of the starting compound; the compounds obtained are listed in the tables below, together with physical data; compounds without these data can be synthesized in a similar manner from the corresponding substances. Because of their close structural relationships with the compounds prepared and investigated, they can be expected to have a similar action.

SYNTHESIS EXAMPLES

I. Preparation of the cyclohexenone oxime ethers I 18.5 g (0.11 mol) of N-hydroxyphthalimide and 31.4 g (0.11 mol) of 1-bromo-[3-(4-bromophenyl)]-prop-2-ene were added in succession to 350 ml of dry N-methylpyrrolidone, and 12.1 g (0.12 mol) of triethylamine were then added dropwise at room temperature. After stirring had been carried out for four days at 20° C., the reaction mixture was poured onto 1.5 l of ice water and the solid was filtered off and washed with water and isopropanol. 34.3 g (86.8% of theory) of N-[3-(4-bromophenyl)-prop-2-enyloxy]-phthalimide with a melting point of 161°–162° C. were obtained.

33.4 g (0.093 mol) of N-[3-(4-bromophenyl)-prop-2-enyloxy]-phthalimide were introduced a little at a time into 50 ml of ethanolamine; the temperature increased to 30° C. After stirring had been carried out for two hours at 60° C., the mixture was allowed to cool and 200 ml of dichloromethane were added to it. It was extracted by shaking with iced water. The organic phase was dried and evaporated down and the residue was crystallized from petroleum ether. 20.2 g (95.3% of theory) of 3-(4-bromophenyl)-prop-2-enyloxyamine of melting point 35°–38° C. were obtained.

3.0 g (0.011 mol) of 2-propionyl-5-(3-tetrahydrothiopyranyl)-cyclohexane- 1,3-dione and 3.0 g (0.013 mol) of 3-(4-bromophenyl)-prop-2-enyloxyamine in 100 ml of methanol were stirred for 16 hours at 20° C. The precipitated reaction product was filtered off under suction at 0° C. and washed with ice cold methanol and petroleum ether. Drying gave 3.7 g (68.4% of theory) of 2-[1-(3-(4-bromophenyl))-prop- 2-enyloximino)-propyl]-3-hydroxy-5-(3-tetrahydrothiopyranyl)-cyclohex-2-en-1-one of melting point 97°–99° C.

TABLE 1

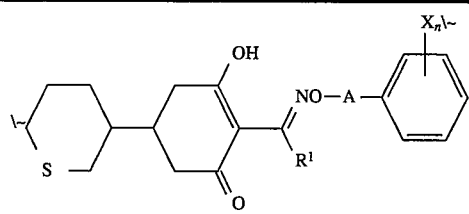

| Example | $R^1$ | A | $X_n$ | Physical data (NMR data in ppm) (mp. in °C.) |
|---|---|---|---|---|
| 1.01 | $C_2H_5$ | $-CH_2-CH=CH-$ | — | 103–104 |
| 1.02 | $n-C_3H_7$ | $-CH_2-CH=CH-$ | — | 4.7(d, 2H), 6.3(dt, 1H), 6.7(d, 1H), 7.2–7.5(2m, 5H) |
| 1.03 | $C_2H_5$ | $-CH_2-CH=CH-$ | 4-Cl | 106–107 |
| 1.04 | $n-C_3H_7$ | $-CH_2-CH=CH-$ | 4-Cl | 4.7(d, 2H), 6.3(dt, 1H), 6.65(d, 1H), 7.2–7.5(m, 4H) |
| 1.05 | $C_2H_5$ | $-CH_2-CH=CH-$ | 4-F | 90–91 |
| 1.06 | $n-C_3H_7$ | $-CH_2-CH=CH-$ | 4-F | 4.6(d, 2H), 6.2(dt, 1H), 6.6(d, 1H), 7.0(m, 2H), 7.4(m, 2H) |
| 1.07 | $C_2H_5$ | $-CH_2-CH=CH-$ | 2,4-$Cl_2$ | 123–124 |
| 1.08 | $n-C_3H_7$ | $-CH_2-CH=CH-$ | 2,4-$Cl_2$ | 80–82 |

TABLE 1-continued

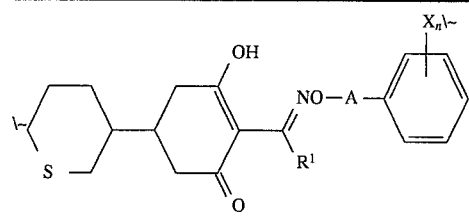

| Example | R¹ | A | $X_n$ | Physical data (NMR data in ppm) (mp. in °C.) |
|---|---|---|---|---|
| 1.09 | $C_2H_5$ | $-(CH_2)_3CH=CH-$ | — | 80–82 |
| 1.10 | $n-C_3H_7$ | $-(CH_2)_3CH=CH-$ | — | 4.1(t, 2H), 6.2(dt, 1H), 6.4(d, 1H), 7.2–7.4(m, 5H) |
| 1.11 | $C_2H_5$ | $-(CH_2)_3CH=CH-$ | 4-Cl | 108–110 |
| 1.12 | $n-C_3H_7$ | $-(CH_2)_3CH=CH-$ | 4-Cl | 4.1(t, 2H), 6.2(dt, 1H), 6.4(d, 1H), 7.3(s, 4H) |
| 1.13 | $C_2H_5$ | $-(CH_2)_3-$ | — | 4.0(t, 2H), 7.0–7.4(m, 5H) |
| 1.14 | $n-C_3H_7$ | $-(CH_2)_3-$ | — | 4.0(t, 2H), 7.0–7.4(m, 5H) |
| 1.15 | $C_2H_5$ | $\backslash -CH_2C(=CH_2)CH_2- \backslash$ | — | 3.3(s, 2H), 4.4(s, 2H), 5.1 and 5.2(2s, 2H), 7.1–7.4(m, 5H) |
| 1.16 | $n-C_3H_7$ | $\backslash -CH_2C(=CH_2)CH_2- \backslash$ | — | 3.35(s, 2H), 4.4(s, 2H), 5.0 and 5.1(2s, 2H), 7.0–7.4(m, 5H) |
| 1.17 | $C_2H_5$ | $-CH_2CH=CH-$ | 4-Br | 89–91 |
| 1.18 | $n-C_3H_7$ | $-CH_2CH=CH-$ | 4-Br | 97–99 |
| 1.19 | $C_2H_5$ | $-CH_2CH=CH-$ | $4-CH_3$ | 103–105 |
| 1.20 | $n-C_3H_7$ | $-CH_2CH=CH-$ | $4-CH_3$ | 88–90 |
| 1.21 | $C_2H_5$ | $-CH_2CH=CH-$ | $4-CF_3$ | 97–98 |
| 1.22 | $n-C_3H_7$ | $-CH_2CH=CH-$ | $4-CF_3$ | 4.75(d, 2H), 6.45(dt, 1H), 6.75(d, 1H), 7.4–7.8(m, 4H) |
| 1.23 | $C_2H_5$ | $-CH_2CH=CH-$ | $4-O-C_6H_5$ | 4.65(d, 2H), 6.25(dt, 1H), 6.65(d, 1H), 6.9–7.6(3m, 9H) |
| 1.24 | $n-C_3H_7$ | $-CH_2CH=CH-$ | $4-O-C_6H_5$ | 4.65(d, 2H), 6.25(dt, 1H), 6.65(d, 1H), 6.9–7.5(3m, 9H) |
| 1.25 | $C_2H_5$ | $-CH_2CH=C(CH_3)-$ | — | 77–78 |
| 1.26 | $n-C_3H_7$ | $-CH_2CH=C(CH_3)-$ | — | 2.15(s, 3H), 4.75(d, 2H), 5.95(t, 1H), 7.2–7.6(m, 5H) |
| 1.27 | $C_2H_5$ | $-CH_2CH=CH-$ | 2-Cl | 97–98 |
| 1.28 | $n-C_3H_7$ | $-CH_2CH=CH-$ | 2-Cl | 87–89 |
| 1.29 | $C_2H_5$ | $-(CH_2)_3-$ | 4-F | 4.05(t, 2H), 6.9–7.2(2m, 4H) |
| 1.30 | $n-C_3H_7$ | $-(CH_2)_3-$ | 4-F | 4.05(t, 2H), 6.9–7.2(2m, 4H) |
| 1.31 | $C_2H_5$ | $-(CH_2)_3-$ | $2,4-Cl_2$ | 63–65 |
| 1.32 | $n-C_3H_7$ | $-(CH_2)_3-$ | $2,4-Cl_2$ | 4.05(t, 2H), 7.05–7.4(2m, 3H) |
| 1.33 | $C_2H_5$ | $-(CH_2)_3-$ | 4-Br | 4.05(t, 2H), 7.05 and 7.45(2m, 4H) |
| 1.34 | $n-C_3H_7$ | $-(CH_2)_3-$ | 4-Br | 4.05(t, 2H), 7.05 and 7.45(2m, 4H) |
| 1.35 | $C_2H_5$ | $-(CH_2)_3-$ | 2-Cl | 4.1(t, 2H), 7.05–7.4(m, 4H) |
| 1.36 | $n-C_3H_7$ | $-(CH_2)_3-$ | 2-Cl | 4.1(t, 2H), 7.05–7.4(m, 4H) |
| 1.37 | $C_2H_5$ | $-(CH_2)_3-$ | 4-Cl | 4.05(t, 2H), 7.0–7.4(m, 4H) |
| 1.38 | $n-C_3H_7$ | $-(CH_2)_3-$ | 4-Cl | 4.05(t, 2H), 7.0–7.4(m, 4H) |
| 1.39 | $C_2H_5$ | $-CH_2CH=CH-$ | $3,5-Cl_2$ | 75–77 |
| 1.40 | $n-C_3H_7$ | $-CH_2CH=CH-$ | $3,5-Cl_2$ | 70–73 |
| 1.41 | $C_2H_5$ | $-CH_2CH_2CH(CH_3)-$ | — | 1.25(d, 3H), 3.95(m, 2H), 7.05–7.4(m, 5H) |
| 1.42 | $n-C_3H_7$ | $-CH_2CH_2CH(CH_3)-$ | — | 1.25(d, 3H), 3.95(m, 2H), 7.05–7.4(m, 5H) |
| 1.43 | $C_2H_5$ | $-(CH_2)_3-$ | $3,5-Cl_2$ | 82–84 |
| 1.44 | $n-C_3H_7$ | $-(CH_2)_3-$ | $3,5-Cl_2$ | 4.05(t, 2H), 7.0–7.25(m, 3H) |
| 1.45 | $C_2H_5$ | $-CH_2CH_2C(=CH_2)-$ | — | 4.15(t, 2H), 5.15(s, 1H), 5.25(s, 1H), 7.2–7.6(m, 5H) |
| 1.46 | $n-C_3H_7$ | $-CH_2CH_2C(=CH_2)-$ | — | 4.15(t, 2H), 5.15(s, 1H), 5.25(s, 1H), 7.2–7.6(m, 5H) |
| 1.47 | $CH_3$ | $-CH_2CH=CH-$ | $2,4-Cl_2$ | 107–108 |
| 1.48 | $CH_3$ | $-CH_2CH=CH-$ | 4-Cl | 104–106 |
| 1.49 | $C_2H_5$ | $-(CH_2)_5-$ | 4-Cl | 4.05(t, 2H), 7.0–7.4(2m, 4H) |
| 1.50 | $n-C_3H_7$ | $-(CH_2)_5-$ | 4-Cl | 64–66 |
| 1.51 | $C_2H_5$ | $-CH_2CH=CH-$ | $3,4-Cl_2$ | 4.7(d, 2H), 6.3(dt, 1H), 6.55(d, 1H), 7.2–7.6(m, 3H) |
| 1.52 | $n-C_3H_7$ | $-CH_2CH=CH-$ | $3,4-Cl_2$ | 4.7(d, 2H), 6.3(dt, 1H), 6.55(d, 1H), 7.2–7.6(m, 3H) |
| 1.53 | $C_2H_5$ | $-CH_2CH(CH_3)CH_2-$ | — | 0.95(d, 3H), 3.9(m, 2H), 7.0–7.5(m, 5H) |
| 1.54 | $n-C_3H_7$ | $-CH_2CH(CH_3)CH_2-$ | — | 0.95(d, 3H), 3.9(m, 2H), 7.0–7.5(m, 5H) |
| 1.55 | $C_2H_5$ | $-(CH_2)_3-$ | $3,4-Cl_2$ | 4.05(t, 2H), 7.0–7.1 and 7.2–7.4(2m, 3H) |
| 1.56 | $n-C_3H_7$ | $-(CH_2)_3-$ | $3,4-Cl_2$ | 4.05(t, 2H), 6.95–7.1 and 7.2–7.45(2m, 3H) |
| 1.57 | $C_2H_5$ | $-CH_2CH(CH_3)CH_2-$ | 4-F | 0.95(d, 3H), 3.9(dd, 2H), 6.8–7.2(m, 4H) |
| 1.58 | $n-C_3H_7$ | $-CH_2CH(CH_3)CH_2-$ | 4-F | 0.95(d, 3H), 3.9(dd, 2H), 6.8–7.2(m, 4H) |
| 1.59 | $C_2H_5$ | $-CH_2CH(CH_3)CH_2-$ | 4-Cl | 0.9(d, 3H), 3.9(m, 2H), 7.0–7.4(2m, 4H) |
| 1.60 | $n-C_3H_7$ | $-CH_2CH(CH_3)CH_2-$ | 4-Cl | 0.9(d, 3H), 3.9(m, 2H), 7.0–7.4(2m, 4H) |
| 1.61 | $C_2H_5$ | $-CH_2CH_2C(CH_3)_2-$ | 4-F | 1.35(s, 6H), 3.85(t, 2H), 7.0 and 7.3(2m, 4H) |
| 1.62 | $n-C_3H_7$ | $-CH_2CH_2C(CH_3)_2-$ | 4-F | 1.35(s, 6H), 3.85(t, 2H), 7.0 and 7.3(2m, 4H) |
| 1.63 | $C_2H_5$ | $-CH_2CH_2C(CH_3)_2-$ | 4-Cl | 1.35(s, 6H), 3.85(t, 2H), 7.25(s, 4H) |
| 1.64 | $n-C_3H_7$ | $-CH_2CH_2C(CH_3)_2-$ | 4-Cl | 1.35(s, 6H), 3.85(t, 2H), 7.25(s, 4H) |
| 1.65 | $C_2H_5$ | $-(CH_2)_6-$ | 4-Cl | 1.15(t, 3H), 4.05(t, 2H), 7.1(d, 2H), 7.25(d, 2H) |
| 1.66 | $n-C_3H_7$ | $-(CH_2)_6-$ | 4-Cl | 0.95(t, 3H), 4.05(t, 2H), 7.1(d, 2H), 7.25(d, 2H) |
| 1.67 | $C_2H_5$ | $-(CH_2)_6-$ | 4-F | 1.1(t, 3H), 4.0(t, 2H) |

TABLE 1-continued

[Structure: cyclohexenone with OH, thiopyran substituent, and oxime ether linkage to substituted phenyl]

| Example | R¹ | A | $X_n$ | Physical data (NMR data in ppm) (mp. in °C.) |
|---|---|---|---|---|
| 1.68 | n-C₃H₇ | —(CH₂)₆— | 4-F | 0.95(t, 3H), 4.0(t, 2H) |
| 1.69 | C₂H₅ | —(CH₂)₅— | 4-F | 1.1(t, 3H), 4.05(t, 2H), 6.95 and 7.1(2m, 4H) |
| 1.70 | n-C₃H₇ | —(CH₂)₅— | 4-F | 0.9(t, 3H), 4.05(t, 2H), 6.95 and 7.1(2m, 4H) |
| 1.71 | C₂H₅ | —CH₂CH(CH₃)—(CH₂)₃— | 2-CH₃ | 2.3(s, 3H), 3.95(t, 1H), 7.1(m, 4H) |
| 1.72 | n-C₃H₇ | —CH₂CH(CH₃)—(CH₂)₃— | 2-CH₃ | 2.3(s, 3H), 3.9(t, 1H), 7.05(m, 4H) |
| 1.73 | n-C₃H₇ | —CH₂CH=CH— | 4-F (Na salt) | 0.8(t, 3H), 4.5(d, 2H), 6.35(dt, 1H), 6.6(d, 1H), 7.0–7.6 (2m, 4H) |
| 1.74 | C₂H₅ | —CH₂CH=CH— | 4-F (Na salt) | 0.8(t, 3H), 4.5(d, 2H) 6.35(dt, 1H), 6.6(d, 1H), 7.0–7.6 (2m, 4H) |
| 1.75 | C₂H₅ | —CH₂CH=CH— | 3-Br | 96–98 |
| 1.76 | n-C₃H₇ | —CH₂CH=CH— | 3-Br | 0.95(t, 3H), 4.65(d, 2H), 6.3(dt, 1H), 6.6(d, 1H), 7.1–7.6 (m, 4H) |
| 1.77 | C₂H₅ | —CH₂CH=CH— | 3-Cl | 98–100 |
| 1.78 | n-C₃H₇ | —CH₂CH=CH— | 3-Cl | 1.0(t, 3H), 4.7(d, 2H), 6.35(dt, 1H), 6.65(d, 1H), 7.2–7.5 (m, 4H) |
| 1.79 | C₂H₅ | —CH₂CH=CH— | 3-F | 77–78 |
| 1.80 | n-C₃H₇ | —CH₂CH=CH— | 3-F | 0.95(t, 3H), 4.65(d, 2H), 6.3(dt, 1H), 6.6(d, 1H), 6.9–7.3 (m, 4H) |
| 1.81 | C₂H₅ | —CH₂CH=CH— | 4-F (benzoate) | 0.95(t, 3H), 4.75(d, 2H), 6.1(dt, 1H), 6.5(d, 1H), 6.9–8.0 (5m, 9H) |
| 1.82 | n-C₃H₇ | —CH₂CH=CH— | 4-F (benzoate) | 0.9(t, 3H), 4.75(d, 2H), 6.1(dt, 1H), 6.4(d, 1H), 6.9–8.0 (5m, 9H) |

TABLE 2

[Structure: cyclohexenone with OH, tetrahydropyran substituent, and oxime ether linkage —NO—A—X—phenyl(Xn)]

| Example | R¹ | A | $X_n$ | Physical data (NMR data in ppm) (mp. in °C.) |
|---|---|---|---|---|
| 2.01 | C₂H₅ | —CH₂—CH=CH— | — | |
| 2.02 | n-C₃H₇ | —CH₂—CH=CH— | — | 4.7(d, 2H), 6.3(dt, 1H), 6.7(d, 1H), 7.2–7.5(2m, 5H) |
| 2.03 | C₂H₅ | —CH₂—CH=CH— | 4-Cl | 106–108 |
| 2.04 | n-C₃H₇ | —CH₂—CH=CH— | 4-Cl | 4.7(d, 2H), 6.3(dt, 1H), 6.65(d, 1H), 7.2–7.5(m, 4H) |
| 2.05 | C₂H₅ | —CH₂—CH=CH— | 4-F | |
| 2.06 | n-C₃H₇ | —CH₂—CH=CH— | 4-F | 4.65(d, 2H), 6.2(dt, 1H), 6.7(d, 1H), 7.0(m, 2H), 7.4(m, 2H) |
| 2.07 | C₂H₅ | —CH₂—CH=CH— | 2,4-Cl₂ | 135–137 |
| 2.08 | n-C₃H₇ | —CH₂—CH=CH— | 2,4-Cl₂ | 4.75(d, 2H), 6.3(dt, 1H), 7.0(d, 1H), 7.05–7.5(2m, 3H) |
| 2.09 | C₂H₅ | —(CH₂)₃CH=CH— | — | 4.1(t, 2H), 6.2(dt, 1H), 6.4(d, 1H), 7.2–7.4(m, 5H) |
| 2.10 | n-C₃H₇ | —(CH₂)₃CH=CH— | — | 4.1(t, 2H), 6.2(dt, 1H), 6.4(d, 1H), 7.1–7.4(m, 5H) |
| 2.11 | C₂H₅ | —(CH₂)₃CH=CH— | 4-Cl | 92–95 |
| 2.12 | n-C₃H₇ | —(CH₂)₃CH=CH— | 4-Cl | 4.1(t, 2H), 6.2(dt, 1H), 6.35(d, 1H), 7.3(s, 4H) |
| 2.13 | C₂H₅ | —(CH₂)₃— | — | 4.05(t, 2H), 7.1–7.4(m, 5H) |
| 2.14 | n-C₃H₇ | —(CH₂)₃— | — | 4.05(t, 2H), 7.1–7.4(m, 5H) |
| 2.15 | C₂H₅ | \——CH₂C(=CH₂)—CH₂—\— | — | 3.35(s, 2H), 4.4(s, 2H), 5.0 and 5.2(2s, 2H), 7.1–7.4(m, 5H) |
| 2.16 | n-C₃H₇ | \——CH₂C(=CH₂)—CH₂—\— | — | 3.35(s, 2H), 4.4(s, 2H), 5.0 and 5.2(2s, 2H), 7.1–7.4(m, 5H) |
| 2.17 | C₂H₅ | —CH₂CH=CH— | 4-Br | 114–116° C. |
| 2.18 | n-C₃H₇ | —CH₂CH=CH— | 4-Br | 99–100° C. |
| 2.19 | C₂H₅ | —CH₂CH=CH— | 4-CH₃ | 123–125 |
| 2.20 | n-C₃H₇ | —CH₂CH=CH— | 4-CH₃ | 70–72 |
| 2.21 | C₂H₅ | —CH₂CH=CH— | 4-CF₃ | 104–106 |

TABLE 2-continued

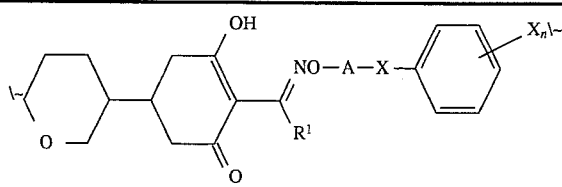

| Example | R¹ | A | $X_n$ | Physical data (NMR data in ppm) (mp. in °C.) |
|---|---|---|---|---|
| 2.22 | n-$C_3H_7$ | $-CH_2CH=CH-$ | 4-$CF_3$ | 4.75(d, 2H), 6.4(dt, 1H), 6.75(d, 1H), 7.4–7.8(m, 4H) |
| 2.23 | $C_2H_5$ | $-CH_2CH=CH-$ | 4-O-$C_6H_5$ | 89–91 |
| 2.24 | n-$C_3H_7$ | $-CH_2CH=CH-$ | 4-O-$C_6H_5$ | 4.65(d, 2H), 6.25(dt, 1H), 6.65(d, 1H), 6.9–7.5(3m, 9H) |
| 2.25 | $C_2H_5$ | $-CH_2CH=C(CH_3)-$ | — | 2.15(s, 3H), 4.75(d, 2H), 5.95(t, 1H), 7.2–7.6(m, 5H) |
| 2.26 | n-$C_3H_7$ | $-CH_2CH=C(CH_3)-$ | — | 2.15(s, 3H), 4.75(d, 2H), 5.95(t, 1H), 7.2–7.6(m, 5H) |
| 2.27 | $C_2H_5$ | $-CH_2CH=CH-$ | 2-Cl | 113–118 |
| 2.28 | n-$C_3H_7$ | $-CH_2CH=CH-$ | 2-Cl | 4.75(d, 2H), 6.3(dt, 1H), 7.05(d, 1H), 7.05–7.6(m, 4H) |
| 2.29 | $C_2H_5$ | $-(CH_2)_3-$ | 4-F | 4.1(t, 2H), 6.9–7.2(2m, 4H) |
| 2.30 | n-$C_3H_7$ | $-(CH_2)_3-$ | 4-F | 4.1(t, 2H), 6.9–7.15(2m, 4H) |
| 2.31 | $C_2H_5$ | $-(CH_2)_3-$ | 2,4-$Cl_2$ | 75–77 |
| 2.32 | n-$C_3H_7$ | $-(CH_2)_3-$ | 2,4-$Cl_2$ | 4.05(t, 2H), 7.05–7.5(2m, 3H) |
| 2.33 | $C_2H_5$ | $-(CH_2)_3-$ | 2-Cl | 4.1(t, 2H), 7.0–7.4(2m, 4H) |
| 2.34 | n-$C_3H_7$ | $-(CH_2)_3-$ | 2-Cl | 4.1(t, 2H), 7.0–7.4(2m, 4H) |
| 2.35 | $C_2H_5$ | $-(CH_2)_3-$ | 4-Cl | 62–64 |
| 2.36 | n-$C_3H_7$ | $-(CH_2)_3-$ | 4-Cl | 4.05(t, 2H), 7.05–7.3(m, 4H) |
| 2.37 | $C_2H_5$ | $-CH_2CH=CH_2-$ | 3,5-$Cl_2$ | 126–127 |
| 2.38 | n-$C_3H_7$ | $-CH_2CH=CH_2-$ | 3,5-$Cl_2$ | 4.7(d, 2H), 6.3(dt, 1H), 6.55(d, 1H), 7.1(m, 3H) |
| 2.39 | $C_2H_5$ | $-(CH_2)_3-$ | 3,5-$Cl_2$ | 79–80 |
| 2.40 | n-$C_3H_7$ | $-(CH_2)_3-$ | 3,5-$Cl_2$ | 4.05(t, 2H), 7.0–7.25(m, 3H) |
| 2.41 | $C_2H_5$ | $-CH_2CH_2C(=CH_2)-$ | — | 4.15(t, 2H), 5.15(s, 1H), 5.3(s, 1H), 7.2–7.5(m, 5H) |
| 2.42 | n-$C_3H_7$ | $-CH_2CH_2C(=CH_2)-$ | — | 4.15(t, 2H), 5.15(s, 1H), 5.3(s, 1H), 7.2–7.5(m, 5H) |
| 2.43 | $CH_3$ | $CH_2CH=CH_2-$ | 4-Br | 135–137 |
| 2.44 | $C_2H_5$ | $-(CH_2)_5-$ | 4-Cl | 66–67 |
| 2.45 | n-$C_3H_7$ | $-(CH_2)_5-$ | 4-Cl | 60–62 |
| 2.46 | $C_2H_5$ | $-CH_2C(CH_3)-CH_2-$ | — | 0.95(d, 3H), 3.9(m, 2H), 7.0–7.4(m, 5H) |
| 2.47 | n-$C_3H_7$ | $-CH_2C(CH_3)-CH_2-$ | — | 0.95(d, 3H), 3.9(m, 2H), 7.0–7.4(m, 5H) |
| 2.48 | $C_2H_5$ | $-CH_2CH=CH_2-$ | 3,4-$Cl_2$ | 4.65(d, 2H), 6.3(dt, 1H), 6.55(d, 1H), 7.2–7.6(m, 3H) |
| 2.49 | n-$C_3H_7$ | $-CH_2CH=CH_2-$ | 3,4-$Cl_2$ | 4.65(d, 2H), 6.3(dt, 1H), 6.55(d, 1H), 7.2–7.6(m, 3H) |
| 2.50 | $C_2H_5$ | $-CH_2C(CH_3)-CH_2-$ | 4-F | 0.95(d, 3H), 3.9(dd, 2H), 6.8–7.2(m, 4H) |
| 2.51 | n-$C_3H_7$ | $-CH_2C(CH_3)-CH_2-$ | 4-F | 0.95(d, 3H), 3.9(dd, 2H), 6.8–7.2(m, 4H) |
| 2.52 | $C_2H_5$ | $-CH_2C(CH_3)-CH_2-$ | 4-Cl | 0.95(d, 3H), 3.9(m with dd, 4H), 7.0–7.4(2m, 4H) |
| 2.53 | n-$C_3H_7$ | $-CH_2C(CH_3)-CH_2-$ | 4-Cl | 0.95(d, 3H), 3.9(m with dd, 4H), 7.0–7.4(2m, 4H) |
| 2.54 | $C_2H_5$ | $-CH_2CH_2C(CH_3)_2-$ | 4-F | 1.3(s, 6H), 3.85(m with t, 4H), 6.9 and 7,3(2m, 4H) |
| 2.55 | n-$C_3H_7$ | $-CH_2CH_2C(CH_3)_2-$ | 4-F | 1.3(s, 6H), 3.85(m with t, 4H), 6.9 and 7,3(2m, 4H) |
| 2.56 | $C_2H_5$ | $-CH_2CH_2C(CH_3)_2-$ | 4-Cl | 1.35(s, 6H), 3.9(m with t, 4H), 7.25(s, 4H) |
| 2.57 | n-$C_3H_7$ | $-CH_2CH_2C(CH_3)_2-$ | 4-Cl | 1.35(s, 6H), 3.9(m mit t, 4H), 7.25(s, 4H) |
| 2.58 | $C_2H_5$ | $-(CH_2)_5-$ | 4-F | 1.1(t, 3H), 4.05(t, 2H), 6.95 and 7.1(2m, 4H) |
| 2.59 | n-$C_3H_7$ | $-(CH_2)_5-$ | 4-F | 0.95(t, 3H), 4.05(t, 2H), 6.95 and 7.1(2m, 4H) |
| 2.60 | $C_2H_5$ | $-CH_2CH=CH-$ | 3-Br | 1.1(t, 3H), 4.65(d, 2H), 6.35(dt, 1H), 6.6(d, 1H), 7.2–7.6(m, 4H) |
| 2.61 | n-$C_3H_7$ | $-CH_2CH=CH-$ | 3-Br | 1.0(t, 3H), 4.65(d, 2H), 6.35(dt, 1H), 6.6(d, 1H), 7.1–7.5(m, 4H) |
| 2.62 | $C_2H_5$ | $-CH_2CH=CH-$ | 3-Cl | 1.1(t, 3H), 4.7(d, 2H), 6.35(dt, 1H), 6.6(d, 1H), 7.2–7.5(m, 4H) |
| 2.63 | n-$C_3H_7$ | $-CH_2CH=CH-$ | 3-Cl | 1.0(t, 3H), 4.7(d, 2H), 6.3(dt, 1H), 6.6(d, 1H), 7.2–7.5(m, 4H) |
| 2.64 | $C_2H_5$ | $-CH_2CH=CH-$ | 3-F | 66–68 |
| 2.65 | n-$C_3H_7$ | $-CH_2CH=CH-$ | 3-F | 1.0(t, 3H), 4.7(d, 2H), 6.3(dt, 1H), 6.6(d, 1H), 6.8–7.4(m, 4H) |

TABLE 3

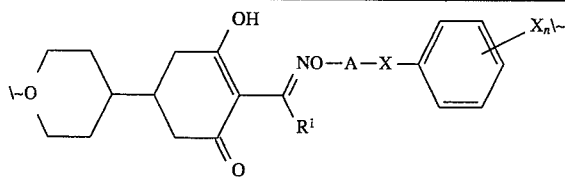

| Example | R¹ | A | $X_n$ | Physical data(NMR data in ppm) (mp. in °C.) |
|---|---|---|---|---|
| 3.01 | $C_2H_5$ | $-CH_2-CH=CH-$ | — | 129–130 |
| 3.02 | n-$C_3H_7$ | $-CH_2-CH=CH-$ | — | 85–87 |
| 3.03 | $C_2H_5$ | $-CH_2-CH=CH-$ | 4-Cl | 130–131 |
| 3.04 | n-$C_3H_7$ | $-CH_2-CH=CH-$ | 4-Cl | 108–110 |
| 3.05 | $C_2H_5$ | $-CH_2-CH=CH-$ | 4-F | 118–120 |
| 3.06 | n-$C_3H_7$ | $-CH_2-CH=CH-$ | 4-F | 87–89 |
| 3.07 | $C_2H_5$ | $-CH_2-CH=CH-$ | 2,4-$Cl_2$ | 95–97 |

TABLE 3-continued

| Example | R¹ | A | $X_n$ | Physical data(NMR data in ppm) (mp. in °C.) |
|---|---|---|---|---|
| 3.08 | n-$C_3H_7$ | —$CH_2$—CH=CH— | 2,4-$Cl_2$ | 93–95 |
| 3.09 | $C_2H_5$ | —$(CH_2)_3$CH=CH— | — | 77–78 |
| 3.10 | n-$C_3H_7$ | —$(CH_2)_3$CH=CH— | — | 67–68 |
| 3.11 | $C_2H_5$ | —$(CH_2)_3$CH=CH— | 4-Cl | 99–100 |
| 3.12 | n-$C_3H_7$ | —$(CH_2)_3$CH=CH— | 4-Cl | 4.05(t, 2H), 6.2(dt, 1H), 6.4(d, 1H), 7.3(s, 4H) |
| 3.13 | $C_2H_5$ | —$(CH_2)_3$— | — | 4.1(t, 2H), 7.0–7.4(m, 5H) |
| 3.14 | n-$C_3H_7$ | —$(CH_2)_3$— | — | 4.1(t, 2H), 7.0–7.4(m, 5H) |
| 3.15 | $C_2H_5$ | \—$CH_2$C(=$CH_2$)$CH_2$—\- | — | 3.4(s, 2H), 4.4(s, 2H), 5.0 and 5.2(2s, 2H), 7.1–7.4(m, 5H) |
| 3.16 | n-$C_3H_7$ | \—$CH_2$C(=$CH_2$)$CH_2$—\- | — | 3.35(s, 2H), 4.4(s, 2H), 5.0 and 5 1(2s, 2H), 7.1–7.4(m, 5H) |
| 3.17 | $C_2H_5$ | —$CH_2$CH=CH | 4-Br | 140–142 |
| 3.18 | n-$C_3H_7$ | —$CH_2$CH=CH | 4-Br | 117–119 |
| 3.19 | $C_2H_5$ | —$CH_2$CH=CH | 4-$CH_3$ | 135–137 |
| 3.20 | n-$C_3H_7$ | —$CH_2$CH=CH | 4-$CH_3$ | 97–98 |
| 3.21 | $C_2H_5$ | —$CH_2$CH=CH | 4-$CF_3$ | 103–104 |
| 3.22 | n-$C_3H_7$ | —$CH_2$CH=CH | 4-$CF_3$ | 114–116 |
| 3.23 | $C_2H_5$ | —$CH_2$CH=CH | 4-O—$C_6H_5$ | 64–66 |
| 3.24 | n-$C_3H_7$ | —$CH_2$CH=CH | 4-O—$C_6H_5$ | 4.65(d, 2H), 6.2(dt, 1H), 6.65(d, 1H), 6.9–7.5(3m, 9H) |
| 3.25 | $C_2H_5$ | —$CH_2$CH=C($CH_3$)— | — | 70–72 |
| 3.26 | n-$C_3H_7$ | —$CH_2$CH=C($CH_3$)— | — | 2.15(s, 3H), 4.75(d, 2H), 5.95(t, 1H), 7.2–7.6(m, 5H) |
| 3.27 | $C_2H_5$ | —$CH_2$CH=CH— | 2-Cl | 85–87 |
| 3.28 | n-$C_3H_7$ | —$CH_2$CH=CH— | 2-Cl | 90–92 |
| 3.29 | $C_2H_5$ | —$(CH_2)_3$— | 4-F | 65–67 |
| 3.30 | n-$C_3H_7$ | —$(CH_2)_3$— | 4-F | 64–66 |
| 3.31 | $C_2H_5$ | —$(CH_2)_3$— | 2,4-$Cl_2$ | 4.05(t, 2H), 7.05–7.4(2m, 3H) |
| 3.32 | n-$C_3H_7$ | —$(CH_2)_3$— | 2,4-$Cl_2$ | 65–67 |
| 3.33 | $C_2H_5$ | —$(CH_2)_3$— | 4-Br | 111–112 |
| 3.34 | $C_2H_5$ | —$(CH_2)_3$— | 2-Cl | 4.1(t, 2H), 7.0–7.4(m, 4H) |
| 3.35 | n-$C_3H_7$ | —$(CH_2)_3$— | 2-Cl | 4.1(t, 2H), 7.05–7.45(m, 4H) |
| 3.36 | $C_2H_5$ | —$(CH_2)_3$— | 4-Cl | 97–99 |
| 3.37 | n-$C_3H_7$ | —$(CH_2)_3$— | 4-Cl | 84–86 |
| 3.38 | $C_2H_5$ | —$CH_2$CH=CH— | 3,5-$Cl_2$ | 127–128 |
| 3.39 | n-$C_3H_7$ | —$CH_2$CH=CH— | 3,5-$Cl_2$ | 80–81 |
| 3.40 | $C_2H_5$ | —$CH_2CH_2$CH($CH_3$)— | — | 1.25(d, 3H), 4.0(m, 2H), 7.05–7.4(m, 5H) |
| 3.41 | n-$C_3H_7$ | —$CH_2CH_2$CH($CH_3$)— | — | 1.25(d, 3H), 4.0(m, 2H), 7.0–7.4(m, 5H) |
| 3.42 | $C_2H_5$ | —$(CH_2)_3$— | 3,5-$Cl_2$ | 105–107 |
| 3.43 | n-$C_3H_7$ | —$(CH_2)_3$— | 3,5-$Cl_2$ | 73–75 |
| 3.44 | $C_2H_5$ | —$CH_2CH_2$C(=$CH_2$)— | — | 4.15(t, 2H), 5.15(s, 1H), 5.3(s, 1H), 7.2–7.6(m, 5H) |
| 3.45 | n-$C_3H_7$ | —$CH_2CH_2$C(=$CH_2$)— | — | 4.15(t, 2H), 5.15(s, 1H), 5.3(s, 1H), 7.2–7.6(m, 5H) |
| 3.46 | $C_2H_5$ | —$(CH_2)_5$— | 4-Cl | 66–67 |
| 3.47 | n-$C_3H_7$ | —$(CH_2)_5$— | 4-Cl | 61–63 |
| 3.48 | $C_2H_5$ | —$CH_2$C($CH_3$)—$CH_2$— | — | 0.9(d, 3H), 3.9(m, 2H), 7.0–7.4(m, 5H) |
| 3.49 | n-$C_3H_7$ | —$CH_2$C($CH_3$)—$CH_2$— | — | 0.9(d, 3H), 3.9(m, 2H), 7.0–7.4(m, 5H) |
| 3.50 | $C_2H_5$ | —$CH_2$CH=CH— | 3,4-$Cl_2$ | 103–105 |
| 3.51 | n-$C_3H_7$ | —$CH_2$CH=CH— | 3,4-$Cl_2$ | 4.65(d, 2H), 6.3(dt, 1H), 6.55(d, 1H), 7.2–7.6(m, 3H) |
| 3.52 | $C_2H_5$ | —$(CH_2)_3$— | 3,4-$Cl_2$ | 3.95–4.1(m, 4H), 7.0–7.1 and 7.2–7.45(2m, 3H) |
| 3.53 | $C_2H_5$ | —$CH_2$C($CH_3$)—$CH_2$— | 4-F | 0.90(d, 3H), 3.85(dd, 2H), 6.8–7.2(m, 4H) |
| 3.54 | n-$C_3H_7$ | —$CH_2$C($CH_3$)—$CH_2$— | 4-F | 0.90(d, 3H), 3.85(dd, 2H), 6.8–7.2(m, 4H) |
| 3.55 | $C_2H_5$ | —$CH_2$C($CH_3$)—$CH_2$— | 4-Cl | 0.90(d, 3H), 3.85(dd, 2H), 7.0–7.4(2m, 4H) |
| 3.56 | n-$C_3H_7$ | —$CH_2$C($CH_3$)—$CH_2$— | 4-Cl | 0.90(d, 3H), 3.85(dd, 2H), 7.0–7.4(2m, 4H) |
| 3.57 | $C_2H_5$ | —$CH_2CH_2$C($CH_3$)$_2$— | 4-F | 1.35(s, 6H), 3.85(t, 2H), 7.0 and 7.3(2m, 4H) |
| 3.58 | n-$C_3H_7$ | —$CH_2CH_2$C($CH_3$)$_2$— | 4-F | 1.35(s, 6H), 3.85(t, 2H), 7.0 and 7.3(2m, 4H) |
| 3.59 | $C_2H_5$ | —$CH_2CH_2$C($CH_3$)$_2$— | 4-Cl | 1.35(s, 6H), 3.85(t, 2H), 7.25(s, 4H) |
| 3.60 | n-$C_3H_7$ | —$CH_2CH_2$C($CH_3$)$_2$— | 4-Cl | 1.35(s, 6H), 3.85(t, 2H), 7.25(s, 4H) |
| 3.61 | $C_2H_5$ | —$(CH_2)_6$— | 4-Cl | 1.15(t, 3H), 3.35(t, 2H), 7.1(d, 2H), 7.25(d, 2H) |
| 3.62 | n-$C_3H_7$ | —$(CH_2)_6$— | 4-Cl | 0.95(t, 3H), 3.35(t, 2H), 7.1(d, 2H), 7.25(d, 2H) |
| 3.63 | $C_2H_5$ | —$(CH_2)_6$— | 4-F | 1.1(t, 3H), 3.35(t, 2H) |
| 3.64 | n-$C_3H_7$ | —$(CH_2)_6$— | 4-F | 0.95(t, 3H), 3.35(t, 2H) |
| 3.65 | $C_2H_5$ | —$(CH_2)_5$— | 4-F | 1.15(t, 3H), 3.35(t, 2H), 6.95 and 7.1(2m, 4m) |
| 3.66 | n-$C_3H_7$ | —$(CH_2)_5$— | 4-F | 0.95(t, 3H), 3.35(t, 2H), 6.95 and 7.1(2m, 4H) |
| 3.67 | $C_2H_5$ | —$CH_2$CH($CH_3$)—$CH_2CH_2CH_2$— | 2-$CH_3$ | 2.3(s, 3H), 7.05(m, 4H) |
| 3.68 | n-$C_3H_7$ | —$CH_2$CH($CH_3$)—$CH_2CH_2CH_2$— | 2-$CH_3$ | 2.3(s, 3H), 7.1(m, 4H) |

TABLE 3-continued

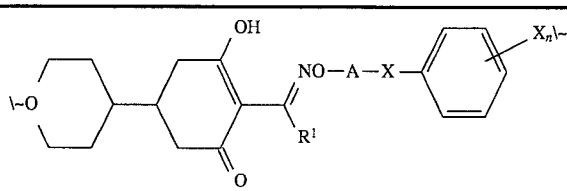

| Example | R¹ | A | $X_n$ | Physical data(NMR data in ppm) (mp. in °C.) |
|---|---|---|---|---|
| 3.69 | n-$C_3H_7$ | —$CH_2CH=CH$— | 3-F | 61–62 |
| 3.70 | $C_2H_5$ | —$CH_2CH=CH$— | 3-Br | 103–105 |
| 3.71 | n-$C_3H_7$ | —$CH_2CH=CH$— | 3-Br | 80–82 |
| 3.72 | $C_2H_5$ | —$CH_2CH=CH$— | 3-Cl | 109–111 |
| 3.73 | n-$C_3H_7$ | —$CH_2CH=CH$— | 3-Cl | 89–91 |
| 3.74 | $C_2H_5$ | —$CH_2CH=CH$— | 3-F | 122–123 |

TABLE 4

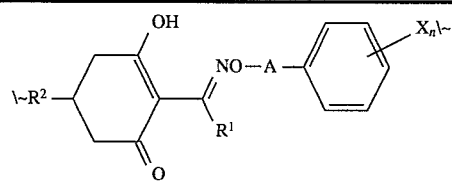

| Example | R² | R¹ | A | $X_n$ | Physical data (NMR data in ppm) (mp. in °C.) |
|---|---|---|---|---|---|
| 4.01 | 2-Ethylthiopropyl | n-$C_3H_7$ | —$(CH_2)_3$— | — | 4.05(t, 2H), 7.15–7.4(m, 5H) |
| 4.02 | 2,4,6-Trimethylphenyl | $C_2H_5$ | —$CH_2CH=CH$— | 2,4-$Cl_2$ | 106–107 |
| 4.03 | 2,4,6-Trimethylphenyl | $C_2H_5$ | —$CH_2CH=CH$— | 4-F | 2.2(s, 3H), 2.35(s, 6H), 4.7(d, 2H), 6.3(dt, 1H), 6.65(d, 1H), 7.0(m, 2H), 7.4(m, 2H) |
| 4.04 | Phenyl | n-$C_3H_7$ | —$CH_2CH=CH$— | 4-F | 55–57 |
| 4.05 | 4-(Benzoylamino)-phenyl | n-$C_3H_7$ | —$CH_2CH=CH$— | 4-F | 80–82 |
| 4.06 | (thiophene ring) | $C_2H_5$ | —$CH_2CH=CH$— | 4-F | 94–96 |
| 4.07 | Cyclohexyl | n-$C_3H_7$ | —$CH_2CH=CH$— | 4-F | 67–69 |
| 4.08 | 3-Isopropyl-isoxazol-5-yl | n-$C_3H_7$ | —$CH_2CH=CH$— | 4-F | 103–104 |
| 4.09 | (thiophene ring) | $C_2H_5$ | —$CH_2CH=CH$— | 2,4-$Cl_2$ | 88–89 |
| 4.10 | Cyclohex-3-enyl | n-$C_3H_7$ | —$CH_2CH=CH$— | 2,4-$Cl_2$ | 75–77 |
| 4.11 | 3-Isopropyl-isoxazol-5-yl | n-$C_3H_7$ | —$CH_2CH=CH$— | 2,4-$Cl_2$ | 113–115 |
| 4.12 | 3-Isopropyl-isoxazol-5-yl | $C_2H_5$ | —$CH_2CH=CH$— | 2,4-$Cl_2$ | 82–83 |
| 4.13 | 4-Ethylphenyl | $C_2H_5$ | —$CH_2CH=CH$— | 2,4-$Cl_2$ | 81–82 |
| 4.14 | 3-Isopropyl-isoxazol-5-yl | $C_2H_5$ | —$CH_2CH=CH$— | 4-F | 98–101 |
| 4.15 | N-Isopopyl-pyrrol-3-yl | n-$C_3H_7$ | —$CH_2CH=CH$— | 4-F | 54–56 |
| 4.16 | 3-Nitro-4-fluor-phenyl | n-$C_3H_7$ | —$CH_2CH=CH$— | 4-Br | 124–126 |
| 4.17 | Cyclohex-3-enyl | n-$C_3H_7$ | —$CH_2CH=CH$— | 4-Br | 68–71 |
| 4.18 | Thien-3-yl | n-$C_3H_7$ | —$CH_2CH=CH$— | 4-Br | 85–87 |
| 4.19 | 4-(Prop-2-inoxy)-phenyl | $C_2H_5$ | —$CH_2CH=CH$— | 4-Br | 126–129 |
| 4.20 | 2-Ethylthiopropyl | $C_2H_5$ | —$CH_2CH=CH$— | 2,4-$Cl_2$ | 4.7(d, 2H), 6.3(dt, 1H), 7.0(d, 1H), 7.2–7.6(m, 3H) |
| 4.21 | 3-Isopropyl isoxazol-5-yl | $CH_3$ | —$CH_2CH=CH$— | 4-Cl | 113–115 |
| 4.22 | Ethoxycarbonyl | n-$C_3H_7$ | —$CH_2CH=CH$— | 4-Cl | 44–45 |
| 4.23 | 4-Ethylphenyl | $C_2H_5$ | —$CH_2CH=CH$— | 4-Cl | 104–106 |

TABLE 4-continued

[Structure: cyclohexenone with OH, R², R¹, N—O—A—phenyl—Xₙ]

| Example | R² | R¹ | A | Xₙ | Physical data (NMR data in ppm) (mp. in °C.) |
|---|---|---|---|---|---|
| 4.24 | [dioxolane-CH group] | C₂H₅ | —CH₂CH=CH— | 4-Cl | 68–70 |
| 4.25 | [cyclohexenyl] | n-C₃H₇ | —CH₂CH=CH— | 4-Cl | 63–64 |
| 4.26 | 4-(Benzoylamino)-phenyl | n-C₃H₇ | —CH₂CH=CH— | 4-Cl | 132–134 |
| 4.27 | 4-(Prop-2-ynyloxy)-phenyl | C₂H₅ | —CH₂CH=CH— | 4-Cl | 122–124 |
| 4.28 | 2-Ethylthiophenyl | n-C₃H₇ | —(CH₂)₆— | 4-Cl | 0.95(t, 3H), 4.0(t, 2H), 7.1(d, 2H), 7.25(d, 2H) |
| 4.29 | 2,4,6-Trimethyl-phenyl | C₂H₅ | —(CH₂)₆— | 4-Cl | 1.15(t, 3H), 2.25(s, 3H), 6.85(s, 2H) |
| 4.30 | 2,4,6-Trimethyl-phenyl | C₂H₅ | —(CH₂)₆— | 4-F | 1.2(t, 3H), 2.25(s, 3H), 4.05(t, 2H) |
| 4.31 | 2-Ethylthiopropyl | n-C₃H₇ | —(CH₂)₆— | 4-F | 0.95(t, 3H), 4.0(t, 2H) |

II Preparation of the hydroxylamines III
E-5-Aminooxy-1-phenyl-1-pentene (Example 5.14)

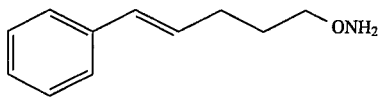

(E)-N-(5-phenyl-4-pentenyloxy)-phthalimide 75.4 g (0.335 mol) of 5-bromo-1-phenyl-1-pentane (prepared by reducing ethyl E-5-phenyl-4-pentanoate with lithium aluminum hydride and treating the alcohol with phosphorus tribromide) were added dropwise to a mixture consisting of 340 ml of N-methylpyrrolidin-2-one, 54.7 g (0.335 mol) of N-hydroxyphthalimide and 5 g of potassium iodide in the course of 30 minutes at 40° C. Stirring was carried out for a further 4 hours at 60° C., the mixture was cooled and then poured into 1.2 l of ice-water, and the solid was filtered off under suction, washed with water and recrystallized from isopropanol. Yield: 91.4 g (89%); mp.: 93°–94° C.;

250-MHz-¹H-NMR (DMSO-d₆): δ (ppm)=1.75–1.95 (m,2H), 2.3–2.5 (m,2H), 4.21 (t,2H), 6.25–6.55 (m,2H), 7.1–7.5 (m,5H), 7.87 (s,4H).

E-5-Aminooxy-1-phenyl-1-pentene 87.8 g (0.286 mol) of the phthalimide ether prepared above were introduced into 130 ml of ethanolamine. After 3 hours at 60° C., the mixture was cooled to room temperature and poured into 200 ml of ice-water. 200 ml of saturated sodium chloride solution were added, after which the title compound was extracted with dichloromethane (three times with 150 ml each time). The combined organic phases were washed with saturated sodium chloride solution (three times with 100 ml each time), dried and evaporated down under reduced pressure. Yield: 40 g (79%);

250-MHz-¹H-NMR (CDCl₃): δ (ppm)=1.7–1.86 (m,2H), 2.2–2.37 (m,2H), 3.72 (t,2H), 5.35 (broad s,2H), 6.1–6.3 (m,1H), 6.4 (d,1H), 7.1–7.4 (m,5H).

The hydroxylamines III shown in Table 5 can be obtained in a similar manner.

TABLE 5

[Structure: H₂N—O—A—phenyl—Xₙ] III

| Example | A | Xₙ | Physical data (mp. °C.) (¹H-NMR data, CDCl₃, ppm) |
|---|---|---|---|
| 5.1 | Prop-2-enylene | — | as hydrochloride 185–190 (decomposition) |
| 5.2 | Prop-2-enylene | 4-Cl | 64–66 |
| 5.3 | Prop-2-enylene | 4-F | 35–40 |
| 5.4 | Prop-2-enylene | 2,4-Cl₂ | 43–47 |
| 5.5 | Prop-2-enylene | 4-CH₃ | 2.35(s, 3H), 4.25(d, 2H)6.2(dt, 1H), 6.6(d, 2H), 7.0–7.4(m, 4H) |
| 5.6 | Prop-2-enylene | 4-CF₃ | 39–41 |
| 5.7 | Prop-2-enylene | 4-phenoxy | 57–58 |
| 5.8 | Prop-2-enylene | 4-Br | 35–38 |
| 5.9 | Propylene | — | as hydrochloride 154–165 |
| 5.10 | Hex-5-enylene | — | |
| 5.11 | Hex-5-enylene | 4-Cl | |
| 5.12 | CH₂—C—CH₂ / CH₂ | — | 3.4(s, 2H)4.1(s, 2H), 4.95(s, 1H), 5.1(s, 1H), 5.3(broads, 2H), 7.1–7.4(m, 5H) |
| 5.13 | 3-Methyl-prop-2-enylene | | 2.1(s, 3H), 4.4(d, 2H), 5.4(broads, |

TABLE 5-continued

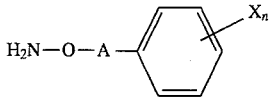

H$_2$N—O—A—[phenyl with X$_n$]  III

| Example | A | X$_n$ | Physical data (mp. °C.) ($^1$H-NMR data, CDCl$_3$, ppm) |
|---|---|---|---|
| 5.14 | Pent-4-ethylene | — | 2H), 5.9 (d, d, 1H), 7.2–7.5(m, 5H) |
| 5.15 | Pent-4-ethylene | 4-Cl | 1.76(m, 2H), 2.28(m, 2H), 3.72(t, 2H), 5.4 (broads, 2H), 6.0–6.5 (m, 2H), 7.23(s, 4H). |
| 5.16 | Propylene | 4-F | |
| 5.17 | Propylene | 2,4-Cl$_2$ | |
| 5.18 | Propylene | 4-Br | |
| 5.19 | Propylene | 2-Cl | |
| 5.20 | Propylene | 4-Cl | |
| 5.21 | Prop-2-enylene | 3,5-Cl$_2$ | |
| 5.22 | —CH$_2$CH$_2$CH(CH$_3$)— | — | |
| 5.23 | Propylene | 3,5-Cl$_2$ | |
| 5.24 | —CH$_2$CH$_2$C(=CH$_2$)— | — | |
| 5.25 | Pentylene | 4-Cl | |
| 5.26 | Prop-2-enylene | 3,4-Cl$_2$ | |
| 5.27 | —CH$_2$CH(CH$_3$)CH$_2$— | — | |
| 5.28 | Propylene | 3,4-Cl$_2$ | |
| 5.29 | —CH$_2$CH(CH$_3$)CH$_2$— | 4-F | |
| 5.30 | —CH$_2$CH(CH$_3$)CH$_2$— | 4-Cl | |
| 5.31 | —CH$_2$CH$_2$C(CH$_3$)CH$_2$— | 4-F | |
| 5.32 | —CH$_2$CH$_2$C(CH$_3$)CH$_2$— | 4-Cl | |
| 5.33 | Hexylene | 4-Cl | |
| 5.34 | Hexylene | 4-F | |
| 5.35 | Pentylene | 4-F | |
| 5.36 | —CH$_2$CH(CH$_3$)—(CH$_2$)$_3$— | 2-CH$_3$ | |
| 5.37 | Prop-2-enylene | 3-Br | |
| 5.38 | Prop-2-enylene | 3-Cl | |
| 5.39 | Prop-2-enylene | 3-F | |

USE EXAMPLES

The herbicidal action of the cyclohexenone oxime ethers of the formula I could be demonstrated by greenhouse experiments:

The culture vessels used were plastic flower pots containing loamy sand with about 3.0% humus as substrate. The seeds of the test plants were sown separately according to species.

In the pre-emergence treatment, the active ingredients suspended or emulsified in water were applied directly after sowing, by means of finely distributing nozzles. The vessels were lightly watered in order to promote germination and growth and were then covered with transparent plastic covers until the plants had begun to grow. This covering ensures uniform germination of the test plants, unless this has been adversely affected by the active ingredients.

For the post-emergence treatment, the test plants were treated with the active ingredients suspended or emulsified in water when they had reached a height of growth of from 3 to 15 cm, depending on the form of growth. The application rate for the post-emergence treatment was 0.25 kg/ha of active substance.

The plants were kept at 10°–25° C. or 20°–35° C., depending on the species. The test period extended over 2 to 4 weeks. During this time, the plants were tended and their reaction to the individual treatments was evaluated.

The evaluation was based on a scale from 0 to 100. 100 means no emergence of the plants or complete destruction of at least the above-ground parts and 0 means no damage or normal growth.

The plants used in the greenhouse experiments consisted of the following species:

| Botanical name | Common name |
|---|---|
| Oryza sativa | rice |
| Echinochloa crus-galli | barnyardgrass |
| Digitaria sanguinalis | — |

0.25 kg/ha of active substance is used in the post-emergence method; Example 1.1 permits very good control of undesirable grassy plants coupled with good toleration by the example crop rice.

We claim:

1. A cyclohexenone oxime ether of the formula

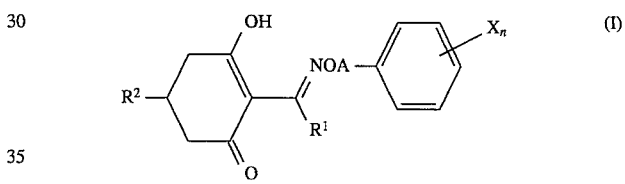

where

R$^1$ is C$_1$–C$_6$-alkyl;

A is a C$_3$-alkylene or C$_3$-alkenylene chain, where these chains may carry one or two methyl groups;

X is halogen;

n is from 0 to 3; 3-tetrahydrothiopyranyl, 3-tetrahydropyranyl or 4-tetrahydropyranyl;

and its agriculturally useful salts and esters of C$_1$–C$_{10}$-carboxylic acids and inorganic acids.

2. A herbicide containing inert additives and a herbicidal amount of one or more compounds of the formula I as claimed in claim 1.

3. A method for controlling undesirable plant growth, wherein the undesirable plants or their habitat is or are treated with a herbicidal amount of a cyclohexenone derivative of the formula I as claimed in claim 1.

* * * * *

UNITED STATES PATENT AND TRADEMARK OFFICE
CERTIFICATE OF CORRECTION

PATENT NO.: 5,563,114

DATED: October 8, 1996

INVENTOR(S): MEYER et al.

It is certified that error appears in the above-identified patent and that said Letters Patent is hereby corrected as shown below:

Column 38, claim 1, line 42, after "n is from 0 to 3;" insert --$R^2$ is --.

Signed and Sealed this

Seventeenth Day of December, 1996

*Attest:*

BRUCE LEHMAN

*Attesting Officer*     *Commissioner of Patents and Trademarks*